(12) United States Patent
Beaurenaut et al.

(10) Patent No.: US 12,013,383 B2
(45) Date of Patent: Jun. 18, 2024

(54) CARBON-BASED GAS SENSING DEVICE AND METHOD FOR OPERATING A CARBON-BASED GAS SENSING DEVICE

(71) Applicant: Infineon Technologies AG, Neubiberg (DE)

(72) Inventors: Laurent Beaurenaut, Neubiberg (DE); Alexandra Marina Roth, Neumarkt (DE); Caterina Travan, Munich (DE); Alexander Zoepfl, Regensburg (DE)

(73) Assignee: INFINEON TECHNOLOGIES AG, Neubiberg (DE)

( * ) Notice: Subject to any disclaimer, the term of this patent is extended or adjusted under 35 U.S.C. 154(b) by 208 days.

(21) Appl. No.: 17/645,627

(22) Filed: Dec. 22, 2021

(65) Prior Publication Data
US 2022/0236245 A1  Jul. 28, 2022

(30) Foreign Application Priority Data

Jan. 22, 2021 (EP) ................................. 21153005

(51) Int. Cl.
*G01N 33/00* (2006.01)
*G01N 27/30* (2006.01)

(52) U.S. Cl.
CPC ....... *G01N 33/0036* (2013.01); *G01N 27/308* (2013.01)

(58) Field of Classification Search
CPC .................................................. G01N 33/0036
USPC ......................................................... 73/23.2
See application file for complete search history.

(56) References Cited

U.S. PATENT DOCUMENTS

| 2004/0147037 | A1 | 7/2004 | Dai et al. |
| 2012/0282594 | A1 | 11/2012 | Chen et al. |
| 2017/0184556 | A1 | 6/2017 | Toffoli et al. |
| 2020/0355662 | A1 | 11/2020 | Carbonelli et al. |
| 2023/0349978 | A1* | 11/2023 | Ponomarev ............. B60L 50/64 |

FOREIGN PATENT DOCUMENTS

| WO | 2009024774 A1 | 2/2009 | |
| WO | WO-2009024774 A1 * | 2/2009 | ............. G08B 17/00 |

OTHER PUBLICATIONS

Seifert, Max et al., "Role of grain boundaries in tailoring electronic properties of polycrystalline graphene by chemical functionalization", 2D Materials, IOP Publishing, 3D Mater. 2, May 6, 2015, 11 pages.

* cited by examiner

*Primary Examiner* — Walter L Lindsay, Jr.
*Assistant Examiner* — Philip T Fadul
(74) *Attorney, Agent, or Firm* — Slater Matsil, LLP

(57) ABSTRACT

A gas sensing device comprises a sensing unit for sensing a target gas, the sensing unit comprising a carbon-based sensing layer which is sensitive to the target gas. The gas sensing device further comprises a controller unit for monitoring an exposure of the sensing layer to the target gas. The controller unit further initializes a recovery sequence for the sensing unit depending on an exposure of the sensing unit to the target gas. Further, the gas sensing device comprises a heating electrode for heating the sensing layer during the recovery sequence.

20 Claims, 14 Drawing Sheets

CARBON-BASED GAS SENSING DEVICE AND METHOD FOR OPERATING A CARBON-BASED GAS SENSING DEVICE

This application claims the benefit of European Patent Application No. 21153005, filed on Jan. 22, 2021, which application is hereby incorporated herein by reference.

TECHNICAL FIELD

Examples of the present disclosure relate to a gas sensing device, in particular a carbon-based gas sensing device. Further examples relate to a method for operating a carbon-based gas sensing device. Examples of the present disclosure relate to a method to desorb gas molecules from graphene sensors in the presence of ozone ($O_3$). Examples of the present disclosure relate to carbon-based multi gas sensors.

BACKGROUND

Awareness of the importance of good air quality is increasing, causing an increasing demand of cheap, small and low power consumption gas sensors for outdoor application. Examples of target gases to be sensed are $NO_2$, $O_3$, $H_2$, CO, and $NH_3$. For example, gas sensor may be applied in monitoring stations as connected elements of a smart city.

The sensors used for air quality monitoring applications are typically chemoresistor gas sensors based on metal oxide (MOX) technology. However, presently, MOX sensors still suffer several drawbacks like sensor aging due to material poising (e.g., siloxane), strong cross sensitivity to humidity and other gases, etc. Thus, those sensors are not very robust and accurate.

An alternative to MOX sensors is provided by graphene-based chemoresistive gas sensors, which make use of graphene as a chemoresistive material. However, graphene material may degrade when exposed to high concentrations of ozone, in particular at a high operation temperature for a certain time period. The ozone exposure may cause strong oxidation in the material increasing the number of functional groups and removing carbon atoms especially from the edge of the graphene structure, as described in M. Seifert et al., 2D Materials, 2, 024008 (2015). This effect may lead to strong changes in the electrical and gas sensing characteristic of the sensor over time. The effects of oxidation may be stronger when the graphene layer is formed by graphene flakes with low lateral dimension, since the reactivity of defect/edges is higher compared to the lower case sp2-hybridized graphene lattice.

SUMMARY

In view of the above described deficiencies of state of the art gas sensing devices, a concept for gas sensing would be desirable, which provides for an improved tradeoff between a low power consumption, an enduringly high sensitivity and a low oxidation of the sensing material.

An example according to the present disclosure provides a gas sensing device. The gas sensing device comprises a sensing unit for sensing a target gas, the sensing unit comprising a carbon-based sensing layer which is sensitive to the target gas. The gas sensing device further comprises a controller unit which is configured for monitoring an exposure of the sensing layer to the target gas. The controller unit is further configured for initializing a recovery sequence for the sensing unit depending on an exposure of the sensing unit to the target gas. Further, the gas sensing device comprises means for heating the sensing layer during the recovery sequence.

Another example of the present disclosure provides a method for operating a carbon-based gas sensing device. The method comprises a step of monitoring an exposure of a sensing unit of the gas sensing device to a target gas. Further, the method comprises a step of initializing a recovery sequence for the sensing unit depending on the exposure of the sensing unit to the target gas. The recovery sequence comprises heating a sensing layer of the sensing unit.

Examples of the present disclosure rely on the idea to initialize a recovery sequence for a sensing unit of a carbon-based gas sensing device in dependence on an exposure of the sensing unit to a target gas to which the sensing unit is sensitive. The recovery sequence includes a heating of a sensing layer of the sensing unit so as to desorb gas molecules from the sensing layer. Initializing the recovery sequence depending on the exposure of the sensing unit to the target gas allows for keeping an oxidation of the sensing layer due to the recovery sequence low. For example, considering the exposure of the sensing unit to the target gas for the initializing of the recovery sequence may allow to reduce the number of recovery sequences while still providing for a high and reliable sensitivity of the sensing unit. In further examples, considering the exposure of the sensing unit to the target gas for the initializing of the recovery sequence allows for reducing the oxidation of the sensing unit during the recovery sequence by choosing a time period for performing the recovery sequence in dependence on an expected exposure to the target gas during the time period.

BRIEF DESCRIPTION OF THE DRAWINGS

Examples of the present disclosure are described herein making reference to the appended figures.

FIG. 9A illustrates a layer of graphene 920. A gas molecule 909 of an electron donor gas, such as $NH_3$, CO, or EthO, adsorbed to the surface of the graphene layer 920 may donate an electron to the graphene layer 920. As graphene may be a p-type conductor, the electrical conductivity may decrease upon adsorption of electron donor gas molecules, as illustrated in FIG. 9B. FIG. 9C illustrates a molecule of an electron acceptor gas, such as $NO_2$, $O_3$, at the resort to the surface of the graphene layer 920. Upon adsorption electron acceptor gas molecules, the electrical conductivity of the graphene layer 920 may increase, as illustrated in FIG. 9D;

FIG. 10A shows normalized sensitivities for four sensing units at a concentration of 100 ppb $NO_2$. The sensing units have been heated to 200° C. for 30 minutes before the measurement of the sensitivities shown in FIG. 10A. FIG. 10B shows corresponding sensitivities for uncleaned sensor's, which have been stored for one week and have not been heated to high temperature. All of the four sensor fields show a lower sensitivity when exposed to $NO_2$ with an uncleaned surface, since most of the adsorption sites are occupied;

FIGS. 11A-11-B a comparison between cleaned an uncleaned sensing units according to a further example. FIG. 11A shows the sensitivity of an example of a sensor unit during a time period during which the concentrations of $NO_2$ and $O_3$, to which the sensing unit is exposed, are modulated.

DETAILED DESCRIPTION OF ILLUSTRATIVE EMBODIMENTS

In the following, embodiments are discussed in detail, however, it should be appreciated that the embodiments provide many applicable concepts that can be embodied in a wide variety of gas sensing applications. The specific embodiments discussed are merely illustrative of specific ways to implement and use the present concept, and do not limit the scope of the embodiments. In the following description, a plurality of details is set forth to provide a more thorough explanation of embodiments of the disclosure. However, it will be apparent to one skilled in the art that other embodiments may be practiced without these specific details. In other instances, well-known structures and devices are shown in form of a block diagram rather than in detail in order to avoid obscuring examples described herein. In addition, features of the different embodiments described herein may be combined with each other, unless specifically noted otherwise.

In the following description of embodiments, the same or similar elements or elements that have the same functionality are provided with the same reference sign or are identified with the same name, and a repeated description of elements provided with the same reference number or being identified with the same name is typically omitted. Hence, descriptions provided for elements having the same or similar reference numbers or being identified with the same names are mutually exchangeable or may be applied to one another in the different embodiments.

Figure 1:
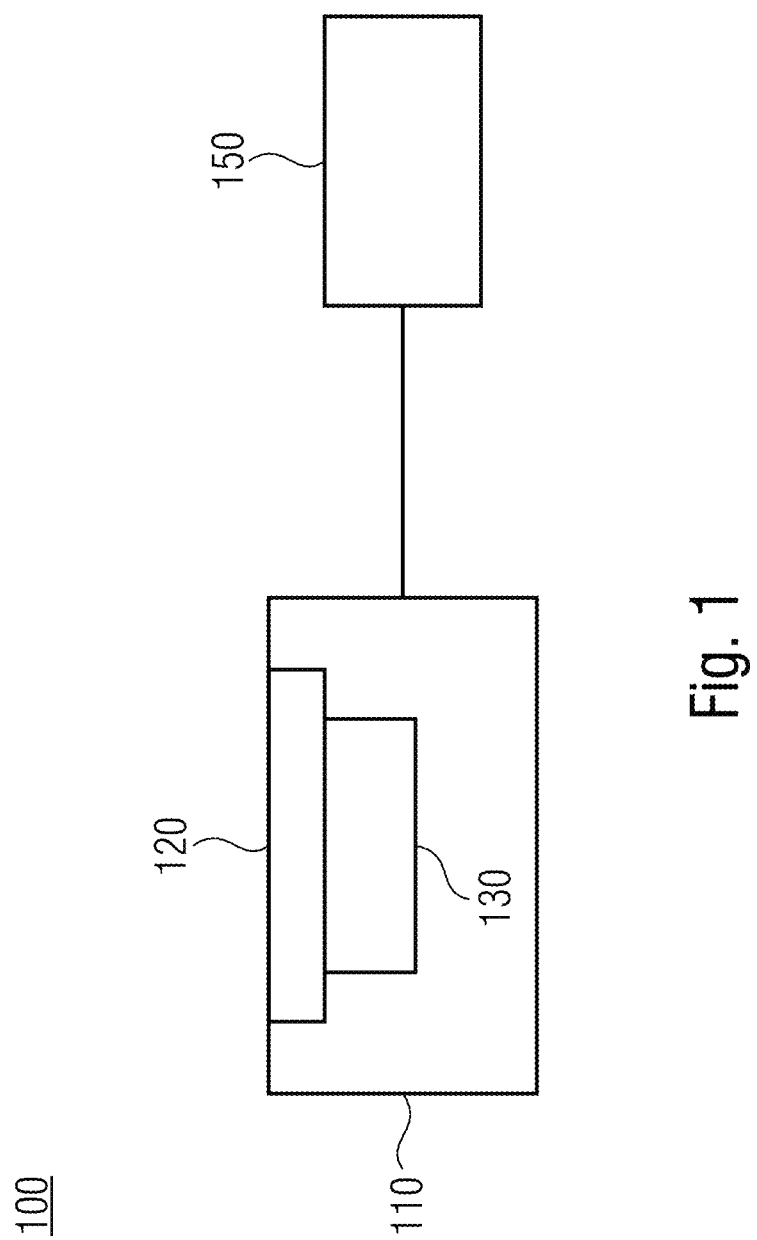
FIG. 1 illustrates an example of a gas sensing device.

FIG. 1 illustrates an example of a gas sensing device boo. The gas sensing device 100 comprises a sensing unit 110 for sensing a target gas. The sensing unit 110 comprises a carbon-based sensing layer 120 which is sensitive to the target gas. The gas sensing device 100 further comprises a controller unit 150 which may be connected with the sensing unit 110. The controller unit 150 is configured for monitoring an exposure of the sensing layer 120 to the target gas. Further, the controller unit 150 is configured for initializing a recovery sequence for the sensing unit 110 depending on the exposure of the sensing unit 110 to the target gas. The gas sensing device further comprises means 130 for heating the sensing layer 120 during the recovery sequence.

For example, during operation of the sensing device 100, the sensing layer 120 is in contact with the environment of the sensing device 100 or a sensing volume of the gas sensing device 100. Gas molecules in the vicinity of the sensing layer 120 may modify electronic properties of the sensing layer 120, providing for a sensitivity of the sensing layer to the target gas. In examples, the sensing layer 120 may be functionalized for the target gas, so that the sensing layer 120 may be particularly sensitive to the target gas.

For example, the target gas may be one of $O_3$, $NO_2$, $H_2$, CO and $NH_3$.

The carbon-based sensing layer 120 comprises a carbon material. For example, the sensing layer 120 comprises one or more of graphene, graphene-oxide and carbon nanotubes.

As the sensing layer 120 is carbon-based, the sensing layer 120 is particularly stable, and therefore hardly affected by structural changes. Therefore, the sensing unit 110 allows for a reliable sensing of the target gas over a long time period. As the sensing layer 120 is carbon-based, it is sensitive to certain target gases, for example $O_3$ and $NO_2$, at room temperature. Therefore, the sensing unit 110 may be operated at a low temperature, e.g. ambient temperature. Compared to MOX sensors, which are usually operated at high temperatures, the sensing unit no may therefore have a lower power consumption. The sensing layer 120 may be particularly stable when comprising graphene.

During operation of the sensing unit 110, gas molecules of the target gas and optionally further gases may be adsorbed at the sensing layer 120. For example, when the sensor is exposed to target gases such as $NO_2$ and/or $O_3$, adsorbed gas molecules accumulate at the sensing layer 120. For high concentrations of accumulated gas molecules at the sensing layer 120, the sensor unit may lose performance. E.g. the sensitivity of the sensing layer 120 may decrease, since many or most of adsorption sites of the sensing material, e.g. graphene, of the sensing layer are occupied. Heating of the sensing layer 120 during the recovery sequence may desorb the accumulated gas molecules from the sensing layer 120, allowing for a restoration of the sensitivity of the sensing layer 120 to a state of a low concentration of adsorbed gas molecules. In other words, the senor may be cleaned by applying a higher temperature cleaning pulse which enhances the desorption of the gas molecules.

However, heating of the sensing layer 120 in the presence of certain gases, e.g. under exposure to $O_3$, may result in an oxidation of the sensing layer 120. For example, at high temperature, $O_3$ may lead to a surface oxidation of the sensing layer 120. Oxidation may result in a degradation of the sensing layer 120. Therefore, operating the sensing unit 110 at a low temperature may enhance the lifetime of the sensing layer 120. Therefore, the sensing unit 110 may be operated at a relatively low temperature, for example ambient temperature, and may be heated during the recovery sequence, the recovery sequence having the aim of desorbing adsorbed gas molecules from the sensing layer 120. By initializing the recovery sequence for the sensing unit 110 depending on the exposure of the sensing unit 110 to the target gas allows for keeping oxidation of the sensing layer 120 during the recovery sequence low.

The exposure of the sensing unit 110 to the target gas, for example $O_3$, may refer to a momentary exposure or, in other examples, may refer to an accumulated exposure of the sensing layer 120 to the target gas over a period of time.

For example, considering a momentary exposure of the sensing layer 120 to the target gas allows for initializing the recovery sequence at a moment at which the exposure of the sensing layer 120 to the target gas is low. Thus, the heating of the sensing layer 120 during the recovery sequence, e.g. during a cleaning pulse, may cause little or no oxidation of the sensing layer 120. Conventional approaches address the problem of oxidation on the system level using redundancy, i.e. a high number of sensing units, in order to improve the overall accuracy and to reduce the error introduced by the degradation of one or few sensors. In contrast, the herein disclosed approach of avoiding oxidation during desorption does not rely on a high number of sensing units, thus providing for a space- and energy efficient gas sensing device which is suitable for consumable applications.

Considering an accumulated exposure of the sensing layer 120 to the target gas allows for initializing the recovery sequence depending on the concentration of accumulated gas molecules at the sensing layer 120. Thus, an operation of the sensing unit 110 at a low sensitivity due to a high concentration of accumulated gas molecules may be avoided. At the same time, an unnecessarily frequent initializing of the recovery sequence may be avoided, such decreasing the risk of a degradation of the sensing layer 120. Conventional approaches try to avoid a loss of performance of chemoresistor gas sensors due to a saturation of the adsorption sites by using high operation temperatures or a temperature modulation where the sensor is heated up to higher temperatures at least for part of the time. The herein disclosed concept of initializing the recovery sequence in dependence on the exposure may reduce the number of recovery sequences and therefore causes lower power consumption (less heating cycles) and lower oxidation of the carbon-based gas sensing device due to surface oxidation caused by $O_3$. Further, a low number of recovery sequences may reduce power consumption, for example in comparison to applying one recovery sequence over several days.

For example, in the case of outdoor sensors, where $O_3$ is always present, the disclosed concept may allow the complete, or at least partial, desorption of the gas molecules and thus the cleaning of the sensor surface. Consequently, the accuracy may be improved and, at the same time, the oxidation rate of the sensor due to the presence of $O_3$ may be reduced to an acceptable level over the lifetime of the gas sensing device.

In examples, the sensing unit 110 is configured for providing a measurement signal in dependence on a concentration of the target gas within an environment to which the sensing layer 120 is exposed. The controller unit 150 may monitor the exposure of the sensing layer 120 to the target gas by evaluating the measurement signal.

For example, the measurement signal provided by the sensing unit may be an analog or a digital signal which may represent the concentration of the target gas in the environment of the sensing layer 120. In examples, the measurement signal may be calibrated for deriving the concentration of the target gas from the measurement signal. The calibration may be performed by the sensing unit 110 or by the controller unit 150. In examples, the controller unit 150 may derive the exposure of the sensing layer 120 to the target gas by using one or more values of the measurement signal or one or more values for the concentration of the target gas, the one or more values being measured at respective instances of time.

In examples, the controller unit 150 may use a further measurement signal of a further sensing unit of the gas sensing device 100 for determining the concentration of the target gas. For example, the controller unit 150 may consider a cross-correlation between the sensing unit and the further sensing unit. The controller unit 150 may use a calibration model for determining the concentration of the target gas based on measurement values of the sensing unit 110 and the further sensing unit.

In examples, the controller unit 150 is configured for determining information about an accumulated exposure of the sensing layer to the target gas over a time period. According to this example, the controller unit 150 is configured for initializing the recovery sequence in dependence on the information about the accumulated exposure.

For example, the controller unit 150 may start an accumulation of the exposure of the sensing layer 120 to the target gas at a time instance at which the operation of the sensing unit 110 is started, or starting after a preceding recovery sequence. When the accumulated exposure of the sensing layer 120 exceeds the threshold, the controller unit 150 may initialize the recovery sequence or may determine a time instance for initializing the recovery sequence.

For example, the information about the accumulated exposure may be determined by accumulating values for the concentration of the target gas, which may be based on the measurement signal of the sensing unit 110 and optionally one or more further sensing units. The information about the accumulated exposure may be determined by integrating the concentration of the target gas over the time period.

In examples, the controller unit 150 is configured for initializing 230 the recovery sequence if the accumulated exposure of the sensing layer 120 to the target gas exceeds a first threshold.

For example, the controller unit may monitor the exposure of the sensing layer 120 to the target gas over time by accumulating the exposure over time. The controller unit may detect whether the exposure exceeds the first threshold and initialize the recovery sequence accordingly.

In examples, the sensing unit 110 comprises one or more further sensing units. Each further sensing unit of the one or more further sensing unit comprises a further sensing layer which is sensitive to a further target gas. The further target gas may be different to the target gas of the sensing unit 110. The gas sensing device may comprise means for heating the one or more further sensing layers during the recovery sequence. Thus, molecules of the target gas adsorbed at the further sensing layers may be desorbed.

For example, the controller unit 150 may consider an exposure of the sensing layer 120 to one or more of the further target gases of the one or more further sensing units for initializing the recovery sequence. For example, the controller unit 150 may determine the information about the accumulated exposure of the sensing layer 120 to the target gas and additionally information about an accumulated exposure of the sensing layer 120 to the further target gas. The controller unit 150 may initialize the recovery sequence, if the exposure of the sensing layer 120 to either of the target gas and the further target gas exceeds a respective first threshold. Alternatively, the controller unit 150 may initialize the recovery sequence, if an accumulated exposure of the sensing layer 120 to the target gas and the further target gas exceeds the first threshold. In other examples, the controller unit 150 may determine information about an accumulated exposure of the sensing layer 120 to the target gas and one or more further target gases.

Thus, in examples, the controller unit 150 is configured for determining information about an accumulated exposure of the sensing layer to the target gas and one or more further target gases over a time period. According to this example, the controller unit 150 is configured for initializing the recovery sequence in dependence on the information about the accumulated exposure.

The control unit 150 may derive the exposure of the sensing layer 120 to the further target gas based on a measurement signal or the concentration of the further target provided by the further sensing unit. The control unit 150 may determine the concentration of the target gas using the measurement signal of the sensing unit 110 and optionally using one or more of the measurement signals provided by the one or more further sensing units. Correspondingly, the control unit 150 may determine the concentration of the further target gas using the measurement signal provided by the further sensing unit and optionally using one or more of the measurement signals provided by the sensing unit 110 and further of the one or more further sensing units. In other words, the gas sensing device 100 may optionally be a multi-gas sensing device.

For example, the target gas and the optionally considered further target gas may be gases which tend to adsorb at the sensing layer 120 at an operation temperature of the sensing unit 110. For example, the target gas may be $O_3$ or $NO_2$.

Figure 2:
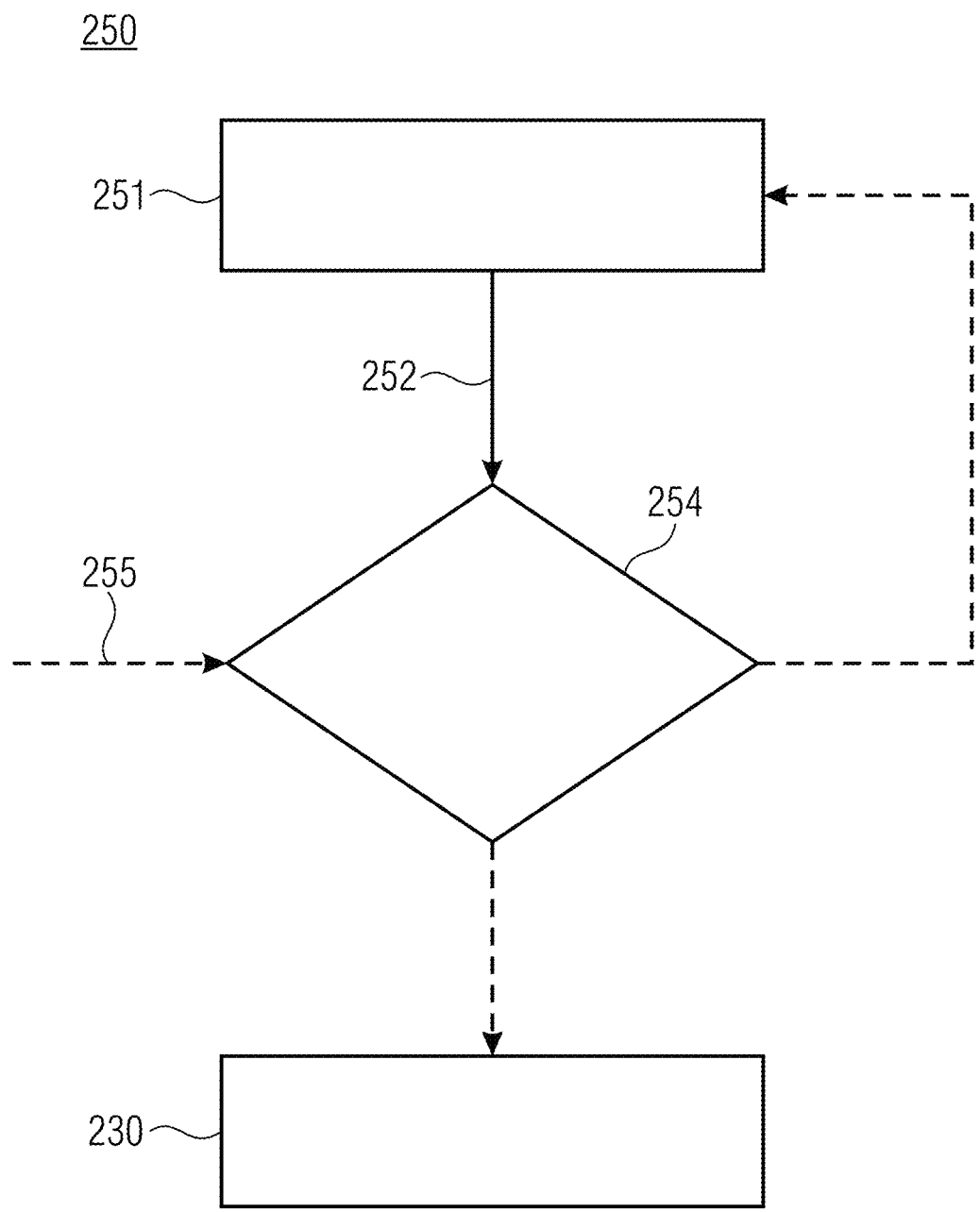
FIG. 2 illustrates an example of an operation scheme for the control unit.

FIG. 2 illustrates a flow chart for an example of an operation scheme 250 of the controller unit 150. For example, the operation scheme 250 may be performed on a processor unit of the controller unit 150. The controller unit 150 may perform a determining 251 of information 252 about an accumulated exposure of the sensing layer 120 to the target gas over a time period. In a step 254 of deciding whether the recovery sequence is to be initialized or not, the controller unit 150 may use the information 252 about the accumulated exposure. If step 254 indicates that the recovery sequence is to be initialized, the controller unit 150 may initialize the recovery sequence in a further step 230. For example, the recovery sequence may be initialized immediately. In alternative examples, further steps may be performed for determining a time instance for initializing the recovery sequence 230, for example, steps 360 and 364 described with respect to FIG. 3 in the following. For example, the recovery sequence is initialized, the $O_3$ concentration is below a certain threshold, e.g. 15 ppb. If step 254 indicates that the recovery sequence is not to be started, the controller unit 150 may proceed with step 251, determining the information about the accumulated exposure for a subsequent time instance by further accumulating the exposure of the sensing layer 120 to the target gas.

Optionally, in step 254, a threshold 255 is evaluated for determining whether the recovery sequence is to be started or not.

Continuing with the description of FIG. 1, in examples, the controller unit 150 is configured for selecting a time instance for initializing the recovery sequence under consideration of an indication for a concentration of a specific target gas at the time instance.

The specific target gas may be a gas which tends to cause oxidation of the sensing layer 120, in particular at high temperatures, for example a temperature used for desorbing the gas molecules during the recovery sequence. For example, the specific target gas is $O_3$. Thus, the specific target gas may be the same gas as the target gas or may be a different gas. Thus, in some examples, the gas sensing device 100 comprises means for obtaining information about a concentration of the specific target gas in the environment of the gas sensing device. For example, the gas sensing device 100 comprises an interface for receiving such information. In further examples, the gas sensing device 100 comprises a further sensing unit having a sensing layer which is sensitive to the specific target gas, e.g. one of the further sensing units as described with respect to FIG. 1. The function of the further sensing unit may be equivalent to the description of the sensing unit 110, however, the sensing unit 110 and the further sensing unit may have different sensitivities to the target gas and to the specific target gas. The further sensing unit may be particularly sensitive to the specific target gas. Thus, the controller unit 150 may determine the exposure of the sensing layer 120 to the specific target gas by using a further measurement signal provided by the further sensing unit, and optionally also using the measurement signal provided by the sensing unit 110.

For example, the controller unit 150 may determine the indication for the concentration of the specific target gas for the time instance based on one or more values for the concentration of the specific target gas, for example using a most recent value for the concentration of the specific target gas. Alternatively, the controller unit 150 may average a plurality of values for the concentration of the specific target gas for determining the indication for the concentration of the specific target gas. In other words, the controller unit 150 may estimate or calculate the indication for the concentration of the specific target gas at the time instance by using values of the concentration of the specific target gas measured during a time period before the time instance, for example during one hour before the time instance.

Figure 3:
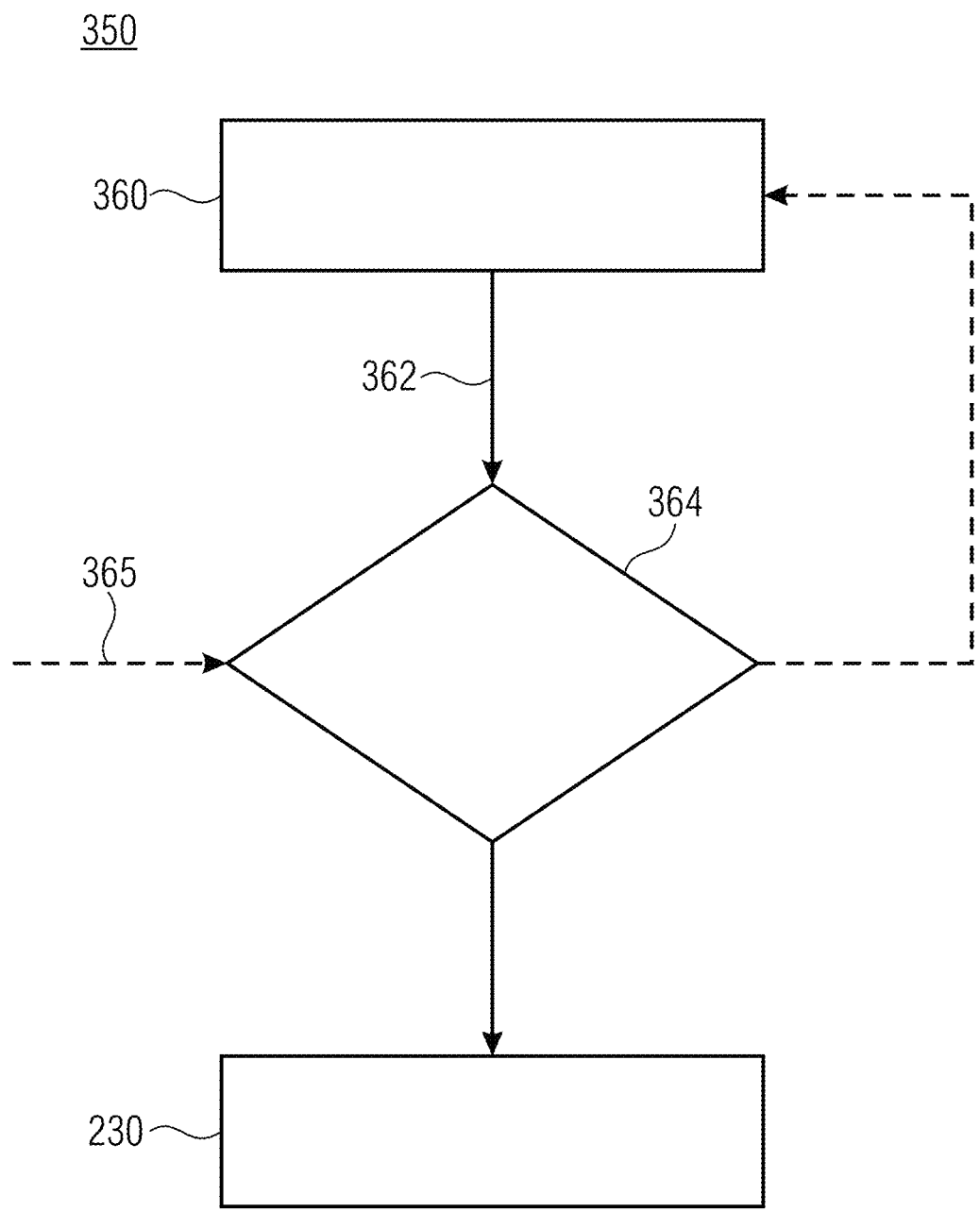
FIG. 3 illustrates another example of an operation scheme for the control unit.

FIG. 3 illustrates a flow chart for an example of an operation scheme 350 of the controller unit 150. The operation scheme 350 may be performed on a processor unit of the controller unit 150. The operation 350 of the controller unit 150 comprises a step 360 of obtaining an indication 362 for a concentration of a specific target gas. According to the operation 350, the controller unit 150 is configured for using the indication 362 for the concentration of the specific target gas for deciding whether to proceed with step 230 of initializing the recovery sequence or not. If step 364 indicates that the recovery sequence is not to be initialized, the controller unit 150 may proceed with step 360, so as to obtain the indication 362 for the concentration of the specific target gas for a subsequent time instance.

For example, in step 364, the controller unit 150 may compare the concentration for the specific target as indicated by the indication 362 with a second threshold 365 and may initialize the recovery sequence, if the concentration of the specific target gas is below the second threshold 365.

It should be noted that the terms first threshold, second threshold, third threshold, etc., are not intended to define an order, for example an order of processing or a temporal order, or a ranking to the thresholds. The terms first threshold, second threshold, third threshold, etc. are rather to be understood as names for distinguishing thresholds used for different purposes.

The operation scheme 250 of FIG. 2 and the operation scheme 350 of FIG. 3 may optionally be combined. Accordingly, the controller unit 150 may be configured for obtaining 360 the indication 362 for the concentration of the specific target gas. If the information 252 about the accumulated exposure indicates that the accumulated exposure of the sensing layer over the time period exceeds the first threshold 255, the controller unit 150 may initialize 230 the recovery sequence at a time for which the indication 362 for the concentration of the specific target gas indicates a concentration of the specific target gas below the second threshold 365.

This example combines the advantages of initializing the recovery sequence when a concentration of accumulated gas molecules at the sensing layer 120 is high and performing the recovery sequence at a time when the concentration of the target gas in the environment of the sensing layer 120 may be low. Therefore, the combination allows for maintaining a high sensitivity of the sensor unit 110, while avoiding oxidation of the sensing layer 120 due to the recovery sequence.

In examples, the controller unit 150 is configured for initializing 230 the recovery sequence, if the information 252 about the accumulated exposure indicates that the accumulated exposure of the sensing layer 120 over the time period exceeds a third threshold.

For example, if the information 252 about the accumulated exposure indicates that the accumulated exposure of the sensing layer 120 over the time period exceeds a third threshold, the controller unit 150 may initialize 230 the recovery sequence irrespective of the indication 362 for the concentration of the specific target gas. That is, the controller unit 150 may perform the step 230 of initializing the recovery sequence, although the concentration of the specific target gas is above the second threshold 365. The third threshold may be higher than the first threshold 255.

Accordingly, the recovery sequence may be performed even if the concentration of the specific target gas does not fall below the second threshold 365. Thus, the consideration of the third threshold may ensure that the recovery sequence may be performed in situations in which the concentration of the specific target gas is continuously above the second threshold 365.

In examples, the control unit 150 is configured for determining information about an oxidation of the sensing layer caused during the recovery sequence.

For an example, the control unit 150 may determine the information about the oxidation of the sensing layer by considering information about a concentration of a gas which causes oxidation of the sensing layer 120, for example the specific target gas.

In continued description of FIG. 1, in examples, the control unit 150 is configured for determining information about an accumulated exposure of the sensing layer 120 to the specific target gas during the recovery sequence. The control unit 150 may initialize a functionality test sequence, if the information about the accumulated exposure to a specific target gas indicates that an accumulated exposure of the sensing layer 120 to the specific target gas during one or more recovery sequences exceeds a fourth threshold.

For example, the information about the accumulated exposure of the sensing layer to the specific target gas during the recovery sequence may be determined based on a measurement signal of the sensing unit 110 and optionally one or more further measurement signals of one or more further sensing units, similar as described with respect to the accumulated exposure to the target gas. The control unit 150 may derive the information about the oxidation of the sensing layer based on the information about the accumulated exposure of the sensing layer to the specific target gas during the recovery sequence. For example, the control unit 150 may conclude from a high accumulated exposure of the sensing layer 120 to the specific target gas during the recovery sequence, that the oxidation of the sensing layer 120 caused during the recovery sequence may be high. The control unit 150 may initialize 230 the recovery sequence, if the accumulated exposure to the specific target gas exceeds the fourth threshold. Optionally, the control unit 150 may accumulate the exposure to the specific target gas during a plurality of recovery sequences, and may initialize 230 the recovery sequence, if the exposure accumulated during a current or the last recovery sequence leads to an exceeding of the fourth threshold by the exposure to the specific target gas accumulated during the plurality of recovery sequences.

The accumulation of the exposure of the sensing layer 120 to the specific target gas may allow to assess real time degradation of the sensing layer 120, and therefore may allow to report a malfunctioning of the sensing unit 110 and/or to correct a model used for the prediction or determination of the concentration of the target gases when the degradation is due to oxidation of the carbon material, e.g. the graphene flakes, of the sensing layer 120 due to long exposure to high concentrations of the specific target gas such as $O_3$.

In examples, the functionality test sequence comprises determining a base line value of the sensing unit. Further, the functionality test sequence may comprise comparing the base line value to one or more previously determined base line values.

The base line value may refer to a measured value of the sensor unit 110, for example the measurement signal or the value of the concentration derived from the measurement signal, as measured in a condition where the concentration of the target gas in the environment of the sensing unit 110 is zero or very low. In examples, it may be difficult to predict when the sensor will be in such a condition. Therefore, examples of the disclosure may make use of the fact that in the case of outdoor gases, this condition is often met during the night when the concentration of certain target gases, e.g., $NO_2$ and $O_3$, are at the lowest. Therefore, in examples, the controller unit 150 may keep track of the state of the sensor in such conditions. For example, the state of the sensor may be characterized by a resistance value. For example, when the sensing material is p-type, as it may be the case for the sensing layer 120 having graphene, a higher resistance value of the sensing layer 120 may indicate if there is a significant increase of the sensor baseline value. An increase of the sensor base line value may be an indication for damages of the structure of the sensing layer 120. For example, the tracking of the state of the sensor may be performed during a time period of some days. Thus, for target gases, which are expected to have a low concentration during specific times of the day, for example during night, several periods, in which these conditions are expected to be met, may be observed. Consequently, an outcome of the functionality test sequence may be more reliable. Thus, the functionality test sequence may last several days, and may be performed in parallel to a normal operation of the sensing unit 110, or any of the other steps described herein.

In examples, the functionality test sequence comprises determining information about a concentration of a further specific target gas, for example $NO_2$, during a specific time period. The functionality test sequence may further comprise comparing the information about the concentration of the further specific target gas to previously determined information about a concentration of the further specific target gas during one or more further specific time periods.

For example, the further specific target gas is a gas, the concentration of which may be expected to follow a specific behavior during the specific time period. For example, the concentration of the specific target gas may be expected to be low or zero during the specific time period. For example, the further specific target gas may be $NO_2$, which may be expected to have a low concentration during the night. If the values of the concentration of $NO_2$ are measured to be particularly high during the hours of the night, this could indicate a malfunctioning of the sensor. For example, the concentration of $NO_2$ during the hours of the night may be evaluated for several days, the reliability of the functionality test sequence. In examples, a malfunctioning of the sensor may be indicated if the concentration measurements of $NO_2$ indicate a concentration higher than 50 ppb during the night for several days. In examples, the further specific target gas may correspond to the target gas.

The functionality test sequence may classify a functionality of the sensing unit 110. For example, the functionality test sequence may indicate that the sensing unit 110 is malfunctioning. For example, a malfunctioning is indicated if the base line value differs from the one or more previously determined base line values or if the concentration of the further specific target gas during the specific time period differs from the concentration of the further specific target gas during the one or more further specific time values or differs from an expected value.

For example, if the functionality test sequence indicates a malfunctioning of the sensing unit 110, that is, if the monitoring of the sensor base line and/or the further specific target gas indicate a sensor degradation, the gas sensing device 100 may notify a malfunction. For example, the supplier and/or the user will may be notified by an alert which allows them to react by either replacing the sensor or updating the sensor's model, for example a calibration model which is used to determine a value of the concentration of the target gas from the measurement signal measured by the sensing unit 110.

In other words, the monitoring of some features of the sensor, e.g. the baseline value of the sensor unit 110 or values for a further specific target gas measured with the sensor unit no, enable the detection of degradation when it occurs. In this case, the sensor may notify a malfunction, thus improving the robustness of the performance of the sensor, since a degradation of the sensor would be detected and possibly corrected. Additionally, the monitoring of the above-mentioned features of the sensor may increase the overall sensor accuracy since the sensor model could be built without the need to include major changes of the sensor characteristics in the model. For example, instead, as changes of the sensor characteristics may be detected, changes may be used as input to the model. In other words, the approach of detecting sensor degradation allows to apply counter measurements and therefore increases the overall robustness of the sensor.

Figure 4:
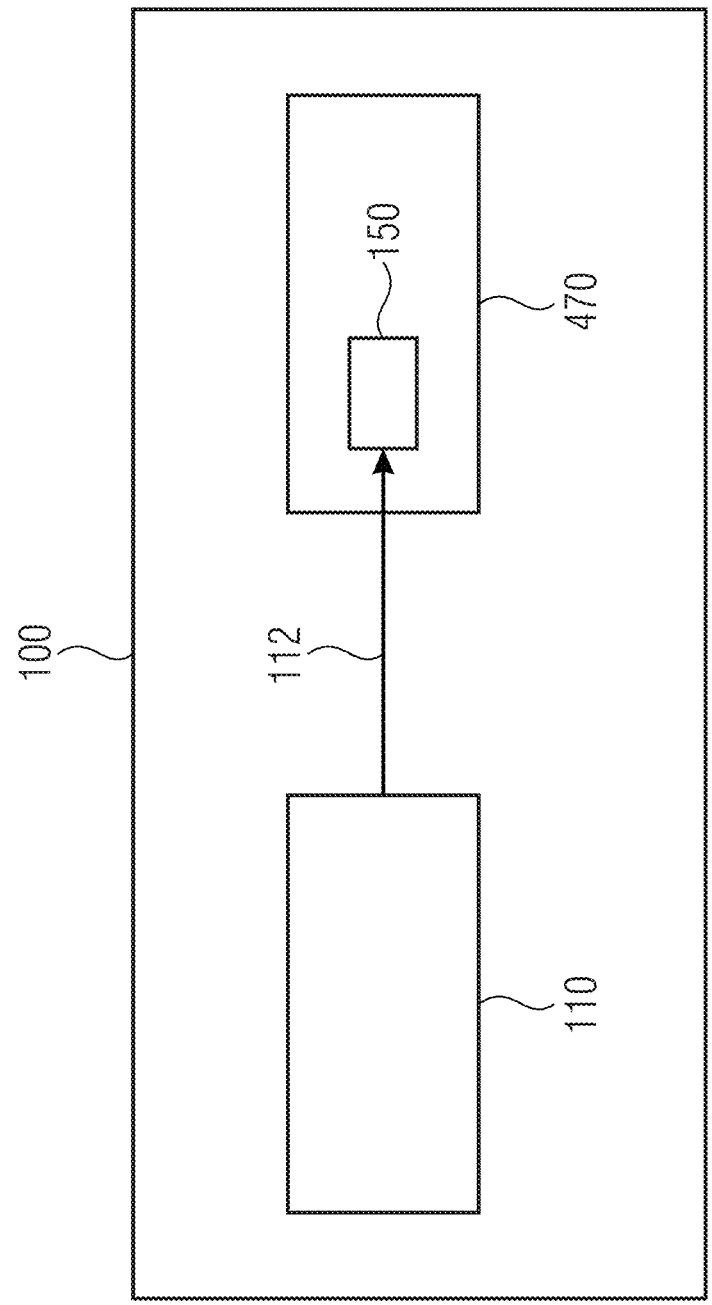
FIG. 4 illustrates another example of the gas sensing device.

FIG. 4 illustrates another example of the gas sensing device 100. According to this example, the sensing unit 110 is configured for providing a measurement signal in dependence on a concentration of the target gas. Further, the gas sensing device 100 comprises a signal calibration unit 470 for determining a calibrated measurement value based on the measurement signal 112. According to this example, the control unit 150 is configured for performing the functionality test sequence in dependence on the accumulated exposure of the sensing layer 120 to the specific target gas during one or more recovery sequences. In the example of FIG. 4, the gas sensing device 100 is configured for adjusting the determination of the calibrated measurement value, if the functionality test sequence indicates a deviation between the base line value and the previously determined base line values, and/or a deviation between the information about the concentration of the further specific target gas and the previously determined information about the concentration of the second specific target gas.

For example, the signal calibration unit 470 may be part of the control unit 150. In other examples, the signal calibration unit 470 may be separate from the control unit 150. In the latter case, the signal calibration unit 470 may be configured for providing the calibrated measurement value to the control unit 150. For example, the control unit 150 may use the calibrated measurement value for determining the exposure of the sensing layer 120 to one or more of the target gas, the specific target gas, and the further specific target gas.

For example, the signal calibration unit 470 may use a calibration model for determining the calibrated measurement value based on the measurement signal. In examples, the calibration model may be a trained model which may rely on calibration data of a plurality of test sensing units like the sensing unit 110. For example, the calibration model may receive as an input the measurement signal and a base line value of the sensor unit 110. The adjusting of the determination of the calibrated measurement value may comprise to update the base line value of the sensing unit 110.

In examples, the recovery sequence comprises heating the sensing layer 120 of the sensing unit 110 to a predetermined temperature which is different from a temperature of the sensing layer 120 during a default operation mode of the gas sensing device.

For example, the default operation mode refers to an operation of the sensing unit 110 different from an operation of the sensing unit during the recovery sequence.

In continued description of FIG. 1, the means 130 for heating the sensing layer 120 may comprise a heating electrode which is thermally coupled with the sensing layer 120, e.g. arranged adjacent to the sensing layer 120. For example, for heating the sensing layer 120, the heating electrode may be heated, e.g., by applying a current to the heating electrode.

Figure 5:
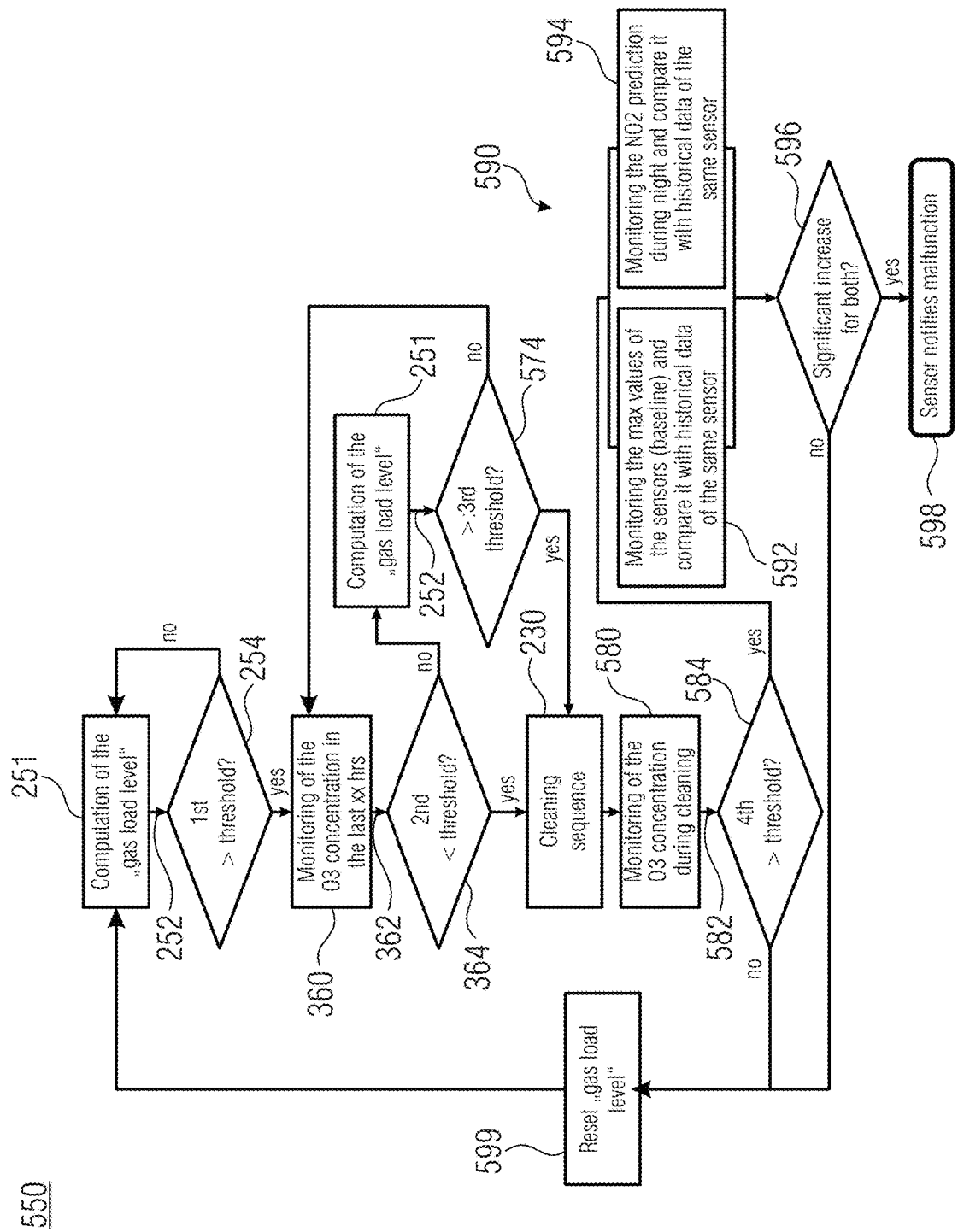
FIG. 5 illustrates another example of an operation scheme for the control unit.

FIG. 5 illustrates another example for an operation scheme 550 of the control unit 150. The operation scheme 550 may be performed on a processor unit of the controller unit 150. The operation scheme 550 may combine the operation schemes 250, 350 of FIGS. 2 and 3 with the feature of using the third threshold for the accumulated exposure of the sensing layer 120 to the target gas and with the feature of the functionality test sequence. Accordingly, in step 251, a gas load level is computed, which may correspond to the information 252 about the accumulated exposure to the target gas. The gas load level may be defined by a cumulated concentration over time. Optionally, beside the target gas, one or more further target gases, e.g. the specific target gas and/or the further specific target gas, are considered for the computation of the gas load level. In examples, the gas load level may represent an accumulated exposure of the sensing layer 120 to $NO_2$ and $O_3$. Thus, the gas load level may be determined on the basis of measurement signals of the sensing unit 110 and one or more further sensing units. According to the example of FIG. 5, the specific target gas is $O_3$. If step 254 indicates that the gas load level 252 is above the first threshold, step 360 is performed which, accordingly, may comprise a determination of the $O_3$ concentration during a preceding time period, so as to determine the indication 362 for the concentration of the specific target gas. For example, the preceding time period is one hour or several hours, or may be less than one hour. In other words, if a first gas loading threshold, i.e. the first threshold, is exceeded, the control unit may determine adequate conditions for issuing a cleaning pulse, i.e. the recovery sequence. For example, an adequate condition may be defined as a moment where the $O_3$ concentration averaged over a certain time period, e.g., one hour, is below the second threshold. If such a condition is met, as may be tested in step 364, the control unit 150 may execute the step 230 of initializing the cleaning sequence. If step 364 indicates that the second threshold is exceeded, the operation scheme proceeds with step 251 of computing the gas load level, for example by further accumulating the concentration of the target gas and optionally one or more further target gases. In a step 574, the gas load level is tested against the third threshold. If the gas load level is below the third threshold, the operation scheme proceeds with step 360, otherwise with step 230 of initializing the cleaning sequence. In other words, if no adequate condition could be found, the cleaning sequence may be executed immediately. During the cleaning sequence, the control unit 150 may perform a monitoring 580 of the $O_3$ concentration so as to determine the information about the accumulated exposure of the sensing layer to the specific target gas during the recovery sequence. Step 580 may, for example, comprise an accumulation of the $O_3$ concentration, e.g., in ppm×hours. The control unit 150 may determine a degradation rate on the basis of the accumulated $O_3$ concentration during the cleaning sequence. In a step 584, the control unit 150 may test whether the degradation rate exceeds the fourth threshold. For example, the control unit 150 may apply a model, e.g., a predefined model, for determining, e.g. based on the accumulated exposure to $O_3$ during the cleaning sequence, whether the degradation rate exceeds the fourth threshold. If the fourth threshold is exceeded, a plausibility check 590 may be performed. The plausibility check 590 may comprise a comparing of historical data of the sensor unit 110 with actual data over a predefined time window. For example, the predefined time window may include the last three days of operation. The plausibility check may be implemented according to the functionality test sequence as described with respect to FIG. 1. Accordingly, the plausibility check 590 may comprise a money touring 592 of maximum values of the sensor unit 110, e.g. baseline values, and compare the maximum values with historical data of the same sensor unit. Additionally or alternatively, the plausibility check 519 may comprise a step 594 of monitoring the $NO_2$ prediction during night and compare it with historical data of the same sensor. In step 596, the control unit may check, whether either the maximum values considered in step 592 or the $NO_2$ prediction considered in step 594 or both of them are increased with respect to the respective historical data. If so, the sender may notify a malfunction, step 598. Otherwise, the gas load level may be reset, step 599, and the operation scheme 550 may restart from the initial step 251.

Figure 6:
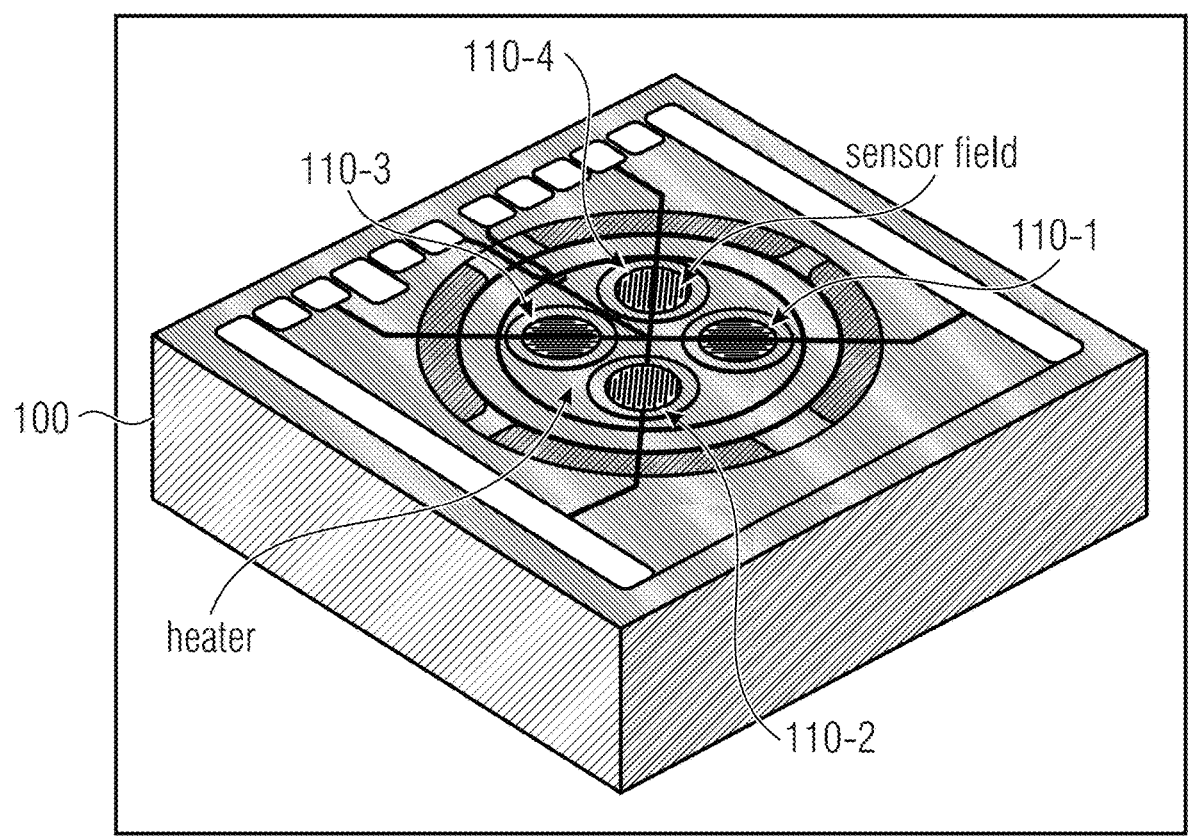
FIG. 6 illustrates another example of the gas sensing device.

FIG. 6 illustrates an example of the sensor device 100. The illustrated example of the sensor device 100 comprises four sensor units 110-1, 110-2, 110-3, 110-4. For example, the sensor unit 110-1 corresponds to the sensor unit 110 and the sensor units of 110-2, 110-3, 110-4 correspond to further sensor units. The sensor units may also be referred to as sensor fields. The sensor device 100 may comprise a heater for heating the sensor units during the recovery sequence. Alternatively, sensor device 100 may comprise respective heaters for the sensor units for heating the sensor units individually, for example to individual temperatures. For example, upon initialization of the recovery sequence, each of the sensor units may be heated, irrespective of the target gas for which the individual sensor units are optimized.

Figure 7:
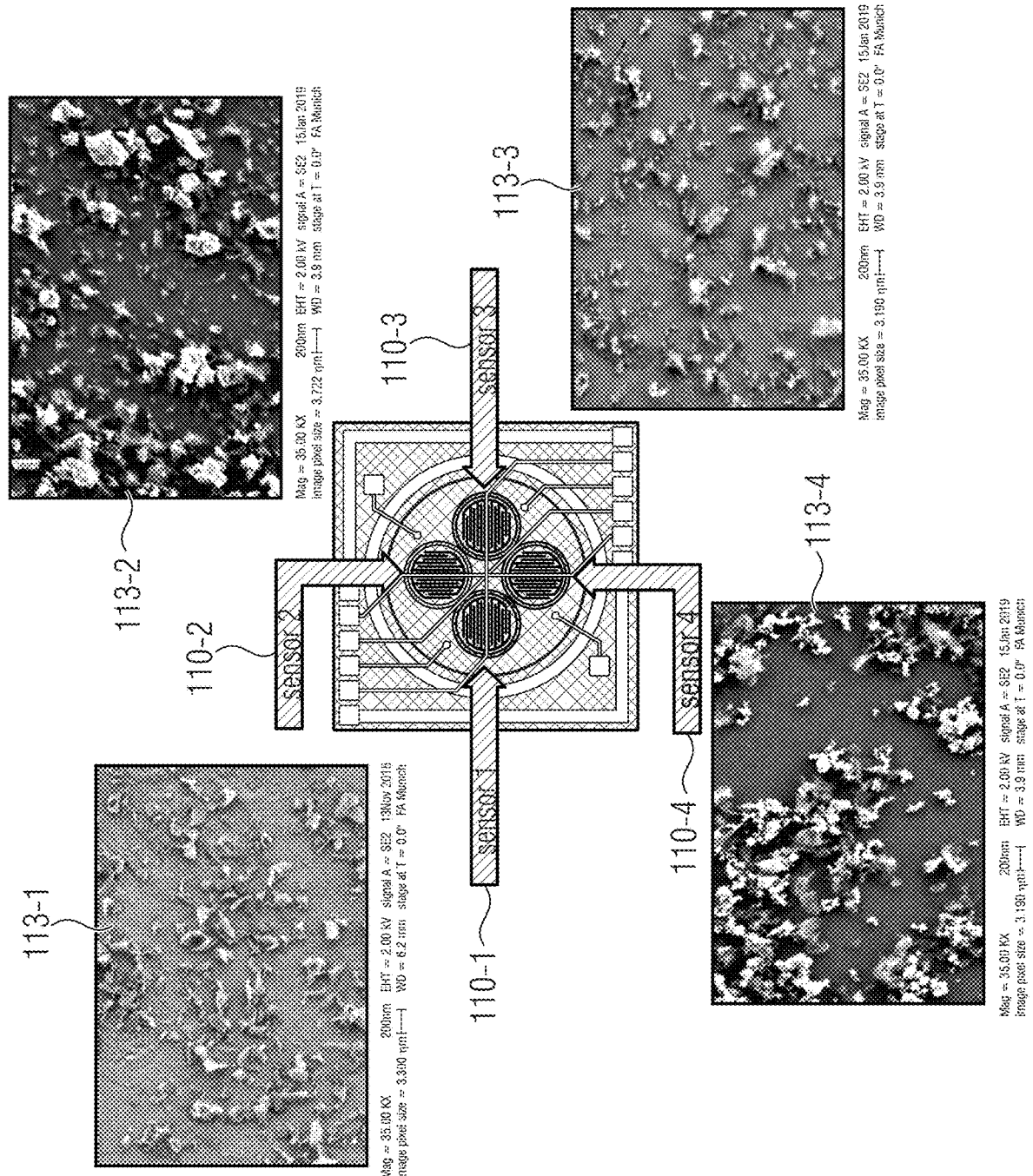
FIG. 7 illustrates examples of surface functionalizations of sensing layers.

FIG. 7 illustrates examples of surface functionalizations 113-1, 113-2, 113-3, 113-4 of sensing layers of the sensor units 110-1, 110-2, 110-3, 110-4. For example, the sensing layer of the sensor unit 110-1 may comprise graphene, plain graphene, e.g. without decoration. Each of the sensing layers of the sensor units 110-2, 110-3, 110-4 may comprise graphene decorated with different metals. Thus, the response of each of the sensor units to a target gas may be different, reducing the cross sensitivity of the sensor. As an alternative to graphene, the sensor units may comprise reduced graphene oxide or carbon nanotubes.

Figure 8:
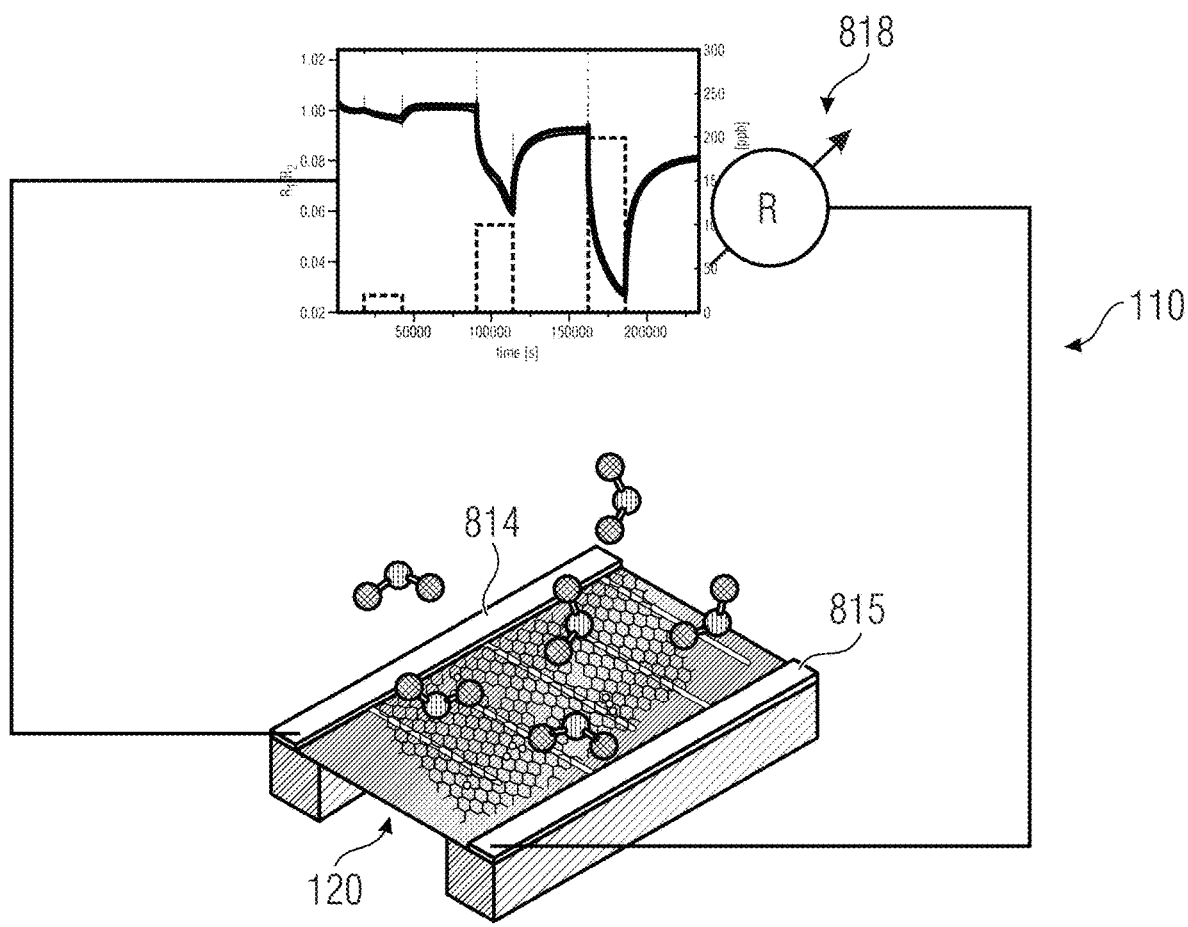
FIG. 8 illustrates an example of the sensing unit.

FIG. 8 illustrates an example of the sensing unit 110. The sensor 100 may comprise a first electrode 814 and a second electrode 815. The sensing layer 120 may be arranged in contact with the first electrode 814 and the second electrode 815 so as to provide an electronic connection between the first electrode and the second electrode. Gas molecules of the target gas adsorbed at the sensing layer 120 may modify the resistivity of the sensing layer. Thus, for example, a resistance measurement 818 may be performed for providing a measurement signal indicating the concentration of the target gas in the environment of the sending unit 110.

Figure 9A:
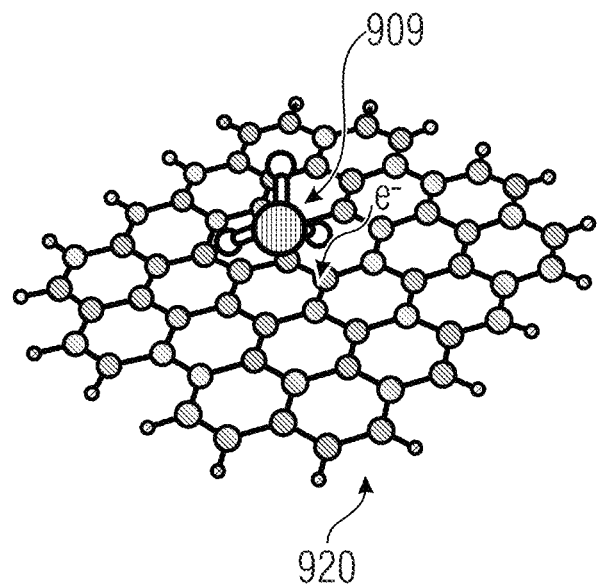
FIGS. 9A-9D illustrate an example of a sensing mechanism of graphene.
Figure 9B:
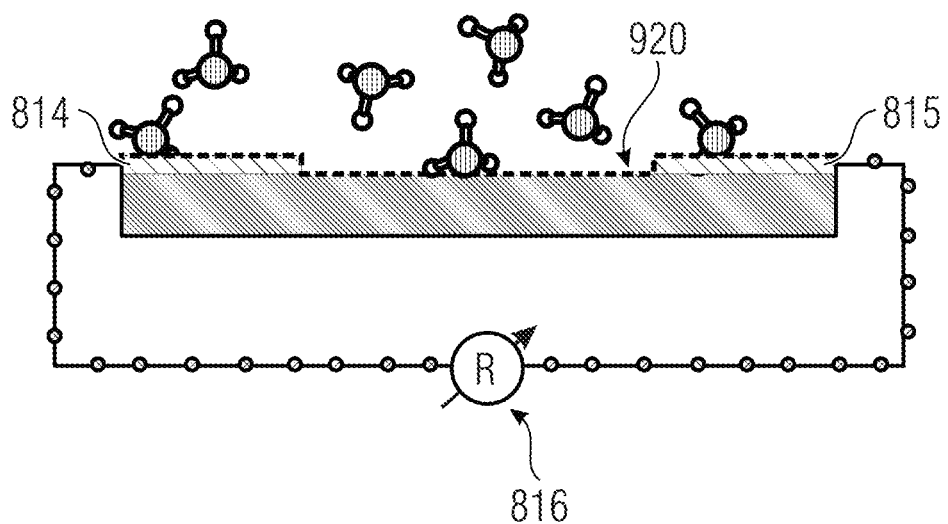
Figure 9C:
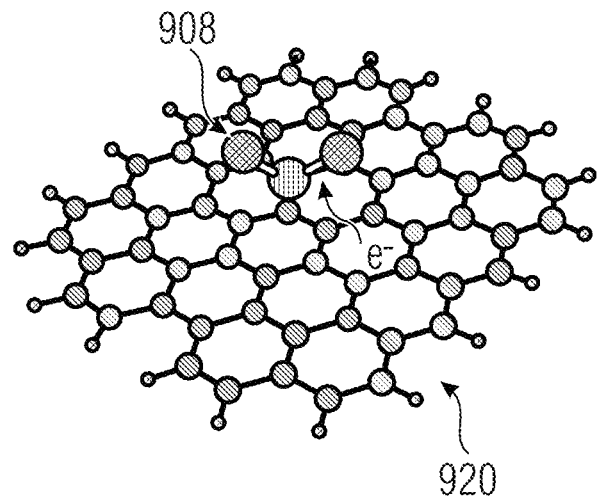
Figure 9D:
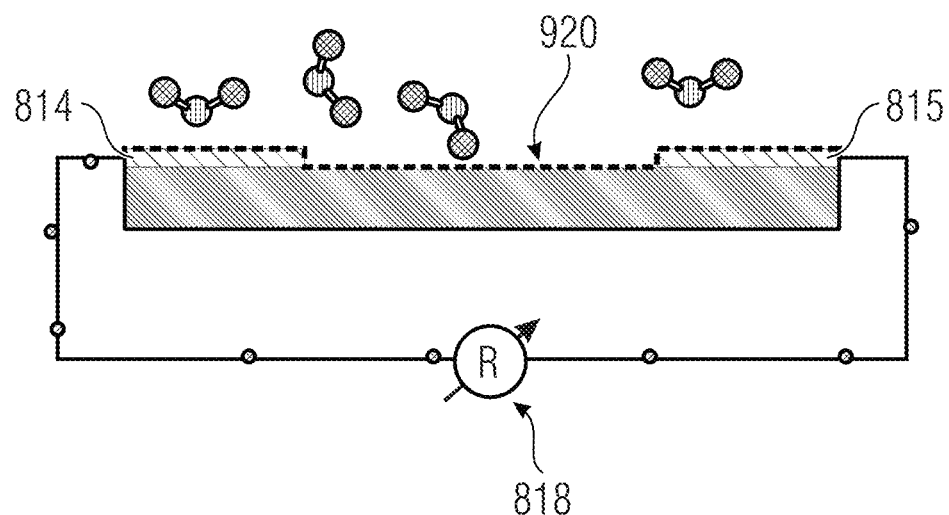

FIGS. 9A-9D illustrate an example of a sensing mechanism of graphene. FIG. 9A illustrates a layer of graphene 920. A gas molecule 909 of an electron donor gas, such as $NH_3$, CO, or EthO, adsorbed to the surface of the graphene layer 920 may donate an electron to the graphene layer 920. As graphene may be a p-type conductor, the electrical conductivity may decrease upon adsorption of electron donor gas molecules, as illustrated in FIG. 9B. FIG. 9C illustrates a molecule of an electron acceptor gas, such as $NO_2$, $O_3$, at the resort to the surface of the graphene layer 920. Upon adsorption electron acceptor gas molecules, the electrical conductivity of the graphene layer 920 may increase, as illustrated in FIG. 9D.

Figure 10A:
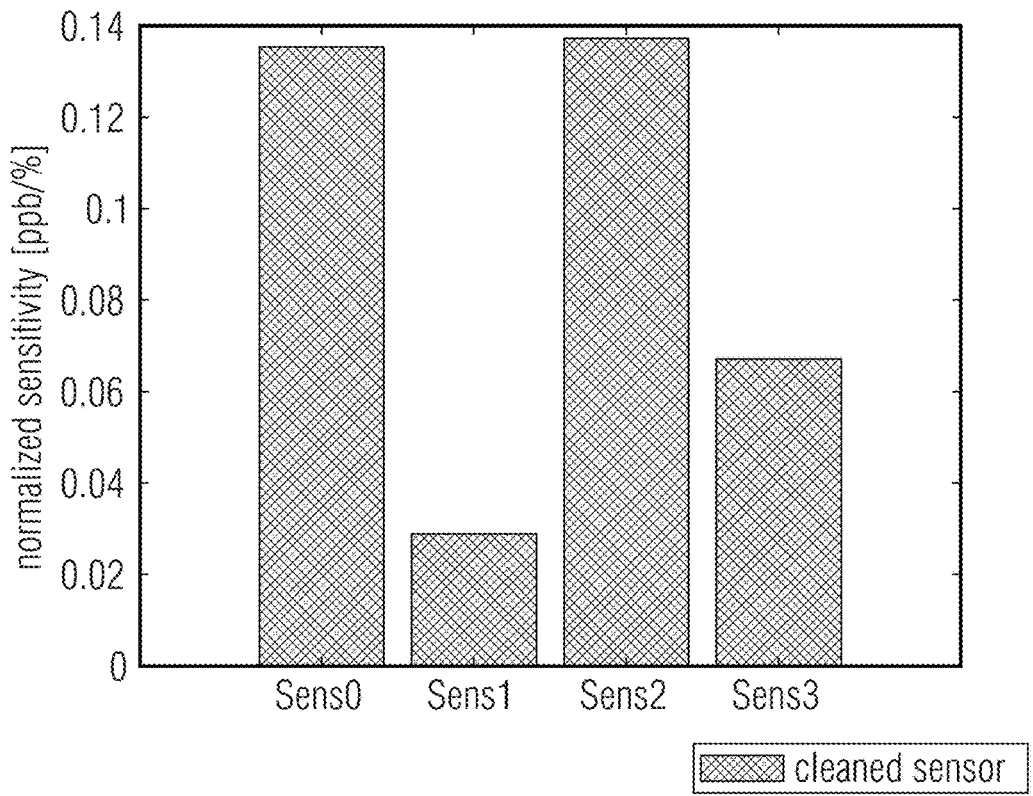
FIGS. 10A-10B a comparison between cleaned and an uncleaned sensing units according to an example.
Figure 10B:
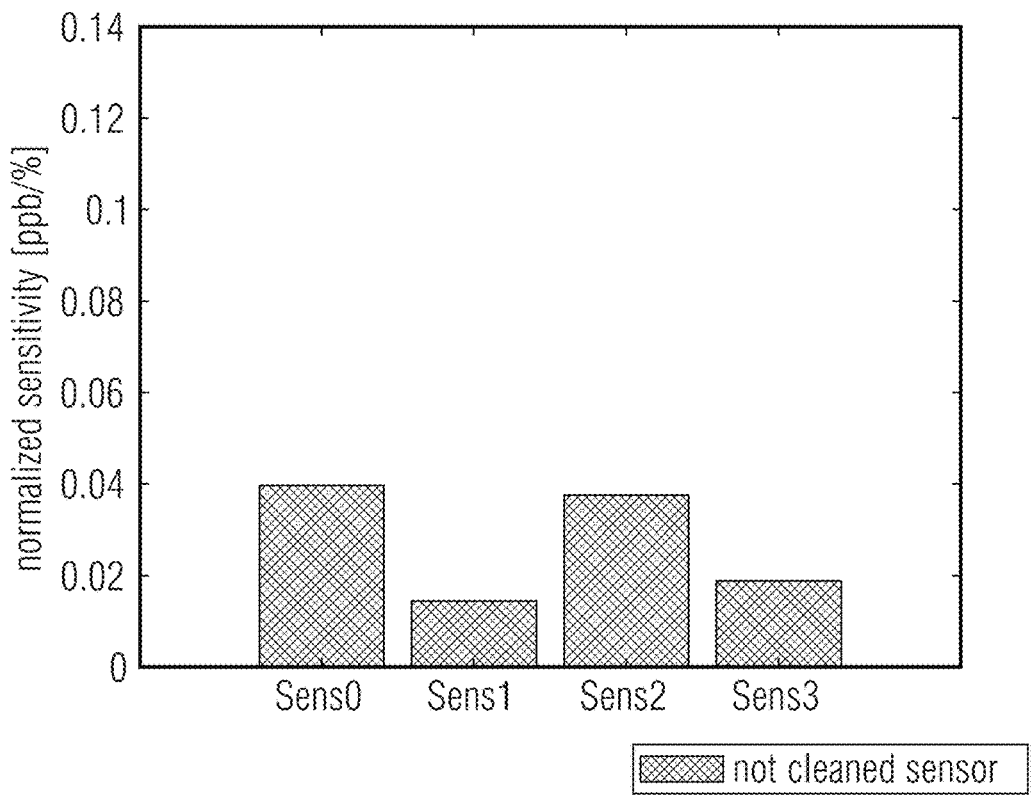

FIGS. 10A-10B illustrate a comparison between cleaned and an uncleaned sensing units according to an example. FIG. 10A shows normalized sensitivities for four sensing units at a concentration of 100 ppb $NO_2$. The sensing units have been heated to 200° C. for 30 minutes before the measurement of the sensitivities shown in FIG. 10A. FIG. 10B shows corresponding sensitivities for uncleaned sensor's, which have been stored for one week and have not been heated to high temperature. All of the four sensor fields show a lower sensitivity when exposed to $NO_2$ with an uncleaned surface, since most of the adsorption sites are occupied.

Figure 11A:
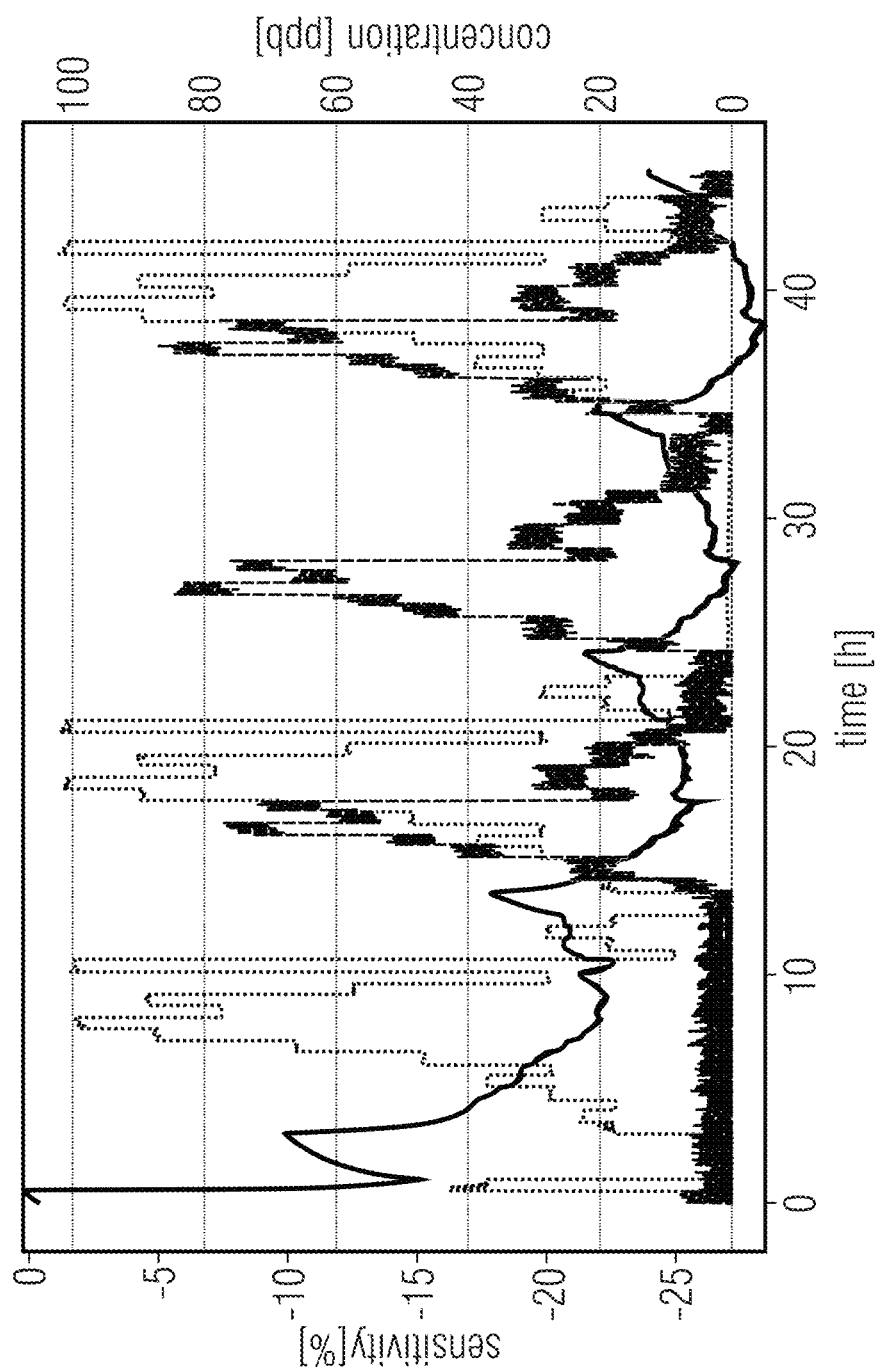
Figure 11B:
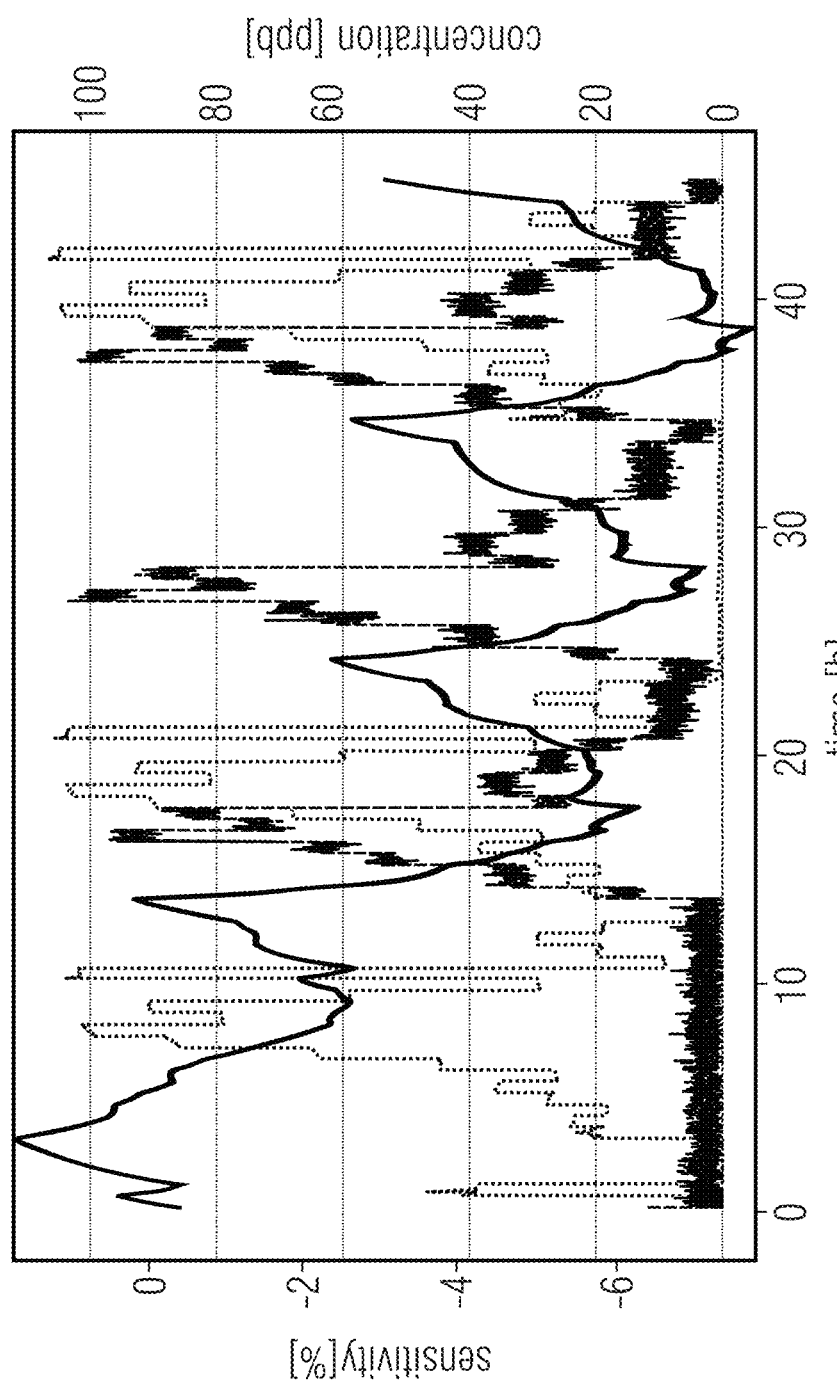
FIG. 11B shows the corresponding sensitivity for an uncleaned sending unit. The decrease of sensitivity upon exposure to $NO_2$ of the cleaned sending unit is higher than the decrease of sensitivity of the sensitivity of the uncleaned sensing unit.

FIGS. 11A-11B illustrate a comparison between cleaned an uncleaned sensing units according to a further example. FIG. 11A shows the sensitivity of an example of a sensor unit during a time period during which the concentrations of $NO_2$ and $O_3$, to which the sensing unit is exposed, are modulated. FIG. 11B shows the corresponding sensitivity for an uncleaned sending unit. The decrease of sensitivity upon exposure to $NO_2$ of the cleaned sending unit is higher than the decrease of sensitivity of the sensitivity of the uncleaned sensing unit.

Figure 12:
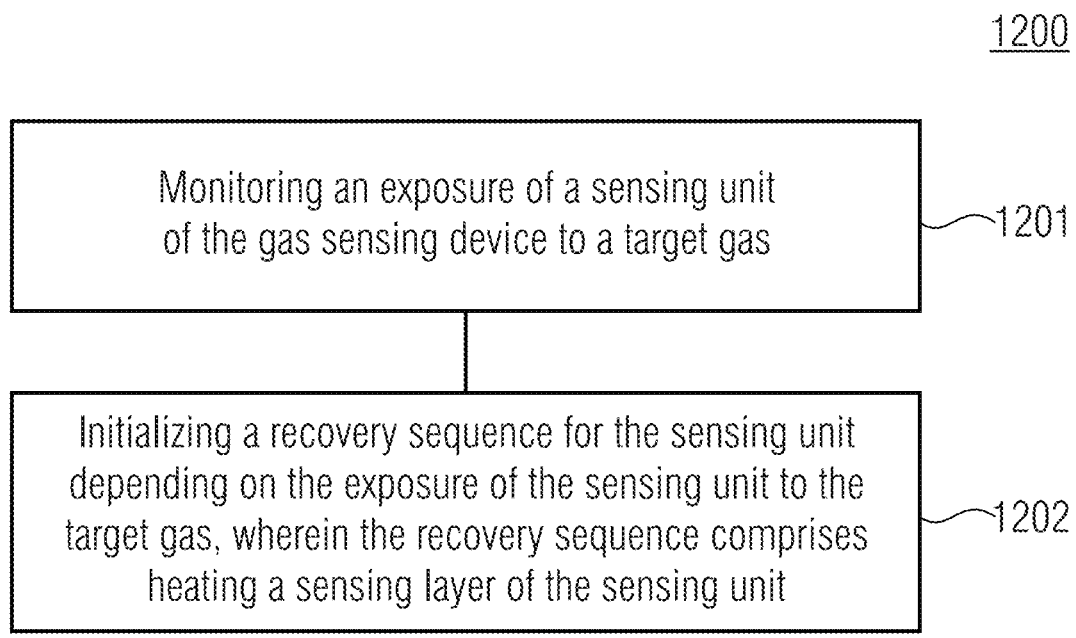
FIG. 12 illustrates a flow chart of an example of a method for operating a carbon-based gas sensing device.

FIG. 12 illustrates a flow chart of an example of a method 1200 for operating a carbon-based gas sensing device. The method 1200 comprises a step 1201 of monitoring and exposure of the sensing unit of the gas sensing device to a target gas. The method 1200 further comprises a step 1202 of initializing a recovery sequence for the sensing unit depending on the exposure of the sensing unit to the target gas. The recovery sequence comprises heating a sensing layer of the sensing unit.

Examples of the present disclosure provide a concept (e.g. a gas sensing device, a method) to clean the surface of the sensor in presence of ozone, the method minimizing the degradation of the sensing layer 120 due to oxidation, while avoiding deterioration of the sensor performance due to saturation effects. Additionally or alternatively, the concept monitors the conditions during cleaning and if certain conditions occur, the sensor will check for possible degradation of its own performance and may notify malfunction of degradation is detected.

The disclosed concept may be implemented in a space-saving module requiring low computational power.

In an alternative approach, the sensor device 100 makes use of an average sensor model which is both including data from degraded samples.

An example of the disclosure provides a gas sensing device 100, comprising:

a sensing unit 110 for sensing a target gas, the sensing unit 110 comprising a carbon-based sensing layer 120 which is sensitive to the target gas, a controller unit 150, configured for monitoring an exposure of the sensing layer 120 to the target gas, and initializing a recovery sequence for the sensing unit 110 depending on the exposure of the sensing unit 110 to the target gas, and means 130 for heating the sensing layer 120 during the recovery sequence.

According to an example, the sensing unit 110 is configured for providing a measurement signal in dependence on a concentration of the target gas within an environment to which the sensing layer 120 is exposed, and the controller unit 150 is configured for monitoring the exposure of the sensing layer 120 to the target gas by evaluating the measurement signal.

According to an example, the controller unit 150 is configured for determining 251 information 252 about an accumulated exposure of the sensing layer 120 to the target gas over a time period, and initializing 230 the recovery sequence in dependence on the information 252 about the accumulated exposure.

According to an example, the controller unit 150 is configured for initializing 230 the recovery sequence if the accumulated exposure of the sensing layer 120 to the target gas exceeds a first threshold.

According to an example, the controller unit 150 is configured for selecting a time instance for initializing 230 the recovery sequence under consideration of an indication 362 for a concentration of a specific target gas at the time instance.

According to an example, the controller 150 unit is configured for initializing 230 the recovery sequence at a time instance for which the indication for the concentration of the specific target gas indicates a concentration of the specific target gas below a second threshold.

According to an example, the controller unit 150 is configured for obtaining 360 an indication 362 for a concentration of a specific target gas, and if the information 252 about the accumulated exposure indicates that the accumulated exposure of the sensing layer 120 over the time period exceeds a first threshold 255, initializing 230 the recovery sequence at a time for which the indication 362 for the concentration of the specific target gas indicates a concentration of the specific target gas below a second threshold 365.

According to an example, the controller unit is configured for initializing 230 the recovery sequence, if the information about the accumulated exposure indicates that the accumulated exposure of the sensing layer over the time period exceeds a third threshold.

According to an example, the control unit 150 is configured for determining information about an oxidation of the sensing layer caused during the recovery sequence.

According to an example, the control unit 150 is configured for determining 580 information 582 about an accumulated exposure of the sensing layer to a specific target gas during the recovery sequence, and initializing a functionality test sequence 590, if the information 582 about the accumulated exposure to the specific target gas indicates, that an accumulated exposure of the sensing layer to the specific target gas during one or more recovery sequences exceeds a fourth threshold.

According to an example, the functionality test sequence 590 comprises determining 592 a baseline value of the sensing unit, and comparing the baseline value to one or more previously determined baseline values.

According to an example, the functionality test sequence 590 comprises determining 594 information about a concentration of a further specific target gas during a specific time period, and comparing the information about the concentration of the further specific target gas to previously determined information about a concentration of the further specific target gas during one or more further specific time periods.

According to an example, the sensing unit 110 is configured for providing a measurement signal 112 in dependence on a concentration of the target gas, and wherein the gas sensing device 100 comprises a signal calibration unit 470 for determining a calibrated measurement value based on the measurement signal, and the gas sensing device 100 is configured for adjusting the determination of the calibrated measurement value if the functionality test sequence indicates a deviation between the baseline value and the previously determined baseline values, and/or a deviation between the information about the concentration of the further specific target gas and the previously determined information about the concentration of the second specific target gas.

According to an example, the recovery sequence comprises heating the sensing layer 120 of the sensing unit 110 to a predetermined temperature which is different from a temperature of the sensing layer during a default operation mode of the gas sensing device 100.

According to an example, the gas sensing device further comprises:

a further sensing unit, the further sensing unit comprising a further sensing layer which is sensitive to a further target gas, and means for heating the further sensing layer during the recovery sequence.

An example of the disclosure provides a method 1200 for operating a carbon-based gas sensing device 100, comprising the following steps:

monitoring 1201 an exposure of a sensing unit of the gas sensing device 100 to a target gas, and initializing 1202 a recovery sequence for the sensing unit depending on the exposure of the sensing unit to the target gas, wherein the recovery sequence comprises heating a sensing layer of the sensing unit.

According to an example, the method 1200 comprises a step of providing a measurement signal in dependence on a concentration of the target gas within an environment to which the sensing layer 120 is exposed. Further, the monitoring of the exposure of the sensing layer 120 to the target gas may comprise evaluating the measurement signal.

According to an example, the method 1200 comprises: determining 251 information 252 about an accumulated exposure of the sensing layer 120 to the target gas over a time period, and further comprises a step of initializing 230 the recovery sequence in dependence on the information 252 about the accumulated exposure.

According to an example, the method 1200 comprises: initializing 230 the recovery sequence if the accumulated exposure of the sensing layer 120 to the target gas exceeds a first threshold.

According to an example, the method 1200 comprises: selecting a time instance for initializing 230 the recovery sequence under consideration of an indication 362 for a concentration of a specific target gas at the time instance.

According to an example, the method 1200 comprises: initializing 230 the recovery sequence at a time instance for which the indication for the concentration of the specific target gas indicates a concentration of the specific target gas below a second threshold.

According to an example, the method 1200 comprises: obtaining 360 an indication 362 for a concentration of a specific target gas. If the information 252 about the accumulated exposure indicates that the accumulated exposure of the sensing layer 120 over the time period exceeds a first threshold 255, the method comprises initializing 230 the recovery sequence at a time for which the indication 362 for the concentration of the specific target gas indicates a concentration of the specific target gas below a second threshold 365.

According to an example, the method 1200 comprises: initializing 230 the recovery sequence, if the information about the accumulated exposure indicates that the accumulated exposure of the sensing layer over the time period exceeds a third threshold.

According to an example, the method 1200 comprises: determining information about a degradation of the sensing layer caused during the recovery sequence.

According to an example, the method 1200 comprises: determining 580 information 582 about an accumulated exposure of the sensing layer to a specific target gas during the recovery sequence. Further, the method comprises: initializing a functionality test sequence 590, if the information 582 about the accumulated exposure to the specific target gas indicates, that an accumulated exposure of the sensing layer to the specific target gas during one or more recovery sequences exceeds a fourth threshold.

According to an example, the functionality test sequence 590 comprises determining 592 a baseline value of the sensing unit, and comparing the baseline value to one or more previously determined baseline values.

According to an example, the functionality test sequence 590 comprises determining 594 information about a concentration of a further specific target gas during a specific time period, and comparing the information about the concentration of the further specific target gas to previously determined information about a concentration of the further specific target gas during one or more further specific time periods.

According to an example, the method 1200 comprises: providing a measurement signal 112 in dependence on a concentration of the target gas, and further comprises a step of determining a calibrated measurement value based on the measurement signal. Further, the method may comprise a step of adjusting the determination of the calibrated measurement value if the functionality test sequence indicates a deviation between the baseline value and the previously determined baseline values, and/or if the functionality test sequence indicates a deviation between the information about the concentration of the further specific target gas and the previously determined information about the concentration of the second specific target gas.

According to an example, the recovery sequence comprises heating the sensing layer 120 of the sensing unit 110 to a predetermined temperature which is different from a temperature of the sensing layer during a default operation mode of the gas sensing device 100.

Although some aspects have been described as features in the context of an apparatus it is clear that such a description may also be regarded as a description of corresponding features of a method. Although some aspects have been described as features in the context of a method, it is clear that such a description may also be regarded as a description of corresponding features concerning the functionality of an apparatus.

Some or all of the method steps may be executed by (or using) a hardware apparatus, like for example, a microprocessor, a programmable computer or an electronic circuit. In some embodiments, one or more of the most important method steps may be executed by such an apparatus.

Depending on certain implementation requirements, embodiments of the invention can be implemented in hardware or in software or at least partially in hardware or at least partially in software. The implementation can be performed using a digital storage medium, for example a floppy disk, a DVD, a Blu-Ray, a CD, a ROM, a PROM, an EPROM, an EEPROM or a FLASH memory, having electronically readable control signals stored thereon, which cooperate (or are capable of cooperating) with a programmable computer system such that the respective method is performed. Therefore, the digital storage medium may be computer readable.

Some embodiments according to the invention comprise a data carrier having electronically readable control signals, which are capable of cooperating with a programmable computer system, such that one of the methods described herein is performed.

Generally, embodiments of the present invention can be implemented as a computer program product with a program code, the program code being operative for performing one of the methods when the computer program product runs on a computer. The program code may for example be stored on a machine readable carrier.

Other embodiments comprise the computer program for performing one of the methods described herein, stored on a machine readable carrier.

In other words, an embodiment of the inventive method is, therefore, a computer program having a program code for performing one of the methods described herein, when the computer program runs on a computer.

A further embodiment of the inventive methods is, therefore, a data carrier (or a digital storage medium, or a computer-readable medium) comprising, recorded thereon, the computer program for performing one of the methods described herein. The data carrier, the digital storage medium or the recorded medium are typically tangible and/or non-transitory.

A further embodiment of the inventive method is, therefore, a data stream or a sequence of signals representing the computer program for performing one of the methods described herein. The data stream or the sequence of signals may for example be configured to be transferred via a data communication connection, for example via the Internet.

A further embodiment comprises a processing means, for example a computer, or a programmable logic device, configured to or adapted to perform one of the methods described herein.

A further embodiment comprises a computer having installed thereon the computer program for performing one of the methods described herein.

A further embodiment according to the invention comprises an apparatus or a system configured to transfer (for example, electronically or optically) a computer program for performing one of the methods described herein to a receiver. The receiver may, for example, be a computer, a mobile device, a memory device or the like. The apparatus or system may, for example, comprise a file server for transferring the computer program to the receiver.

In some embodiments, a programmable logic device (for example a field programmable gate array) may be used to perform some or all of the functionalities of the methods described herein. In some embodiments, a field programmable gate array may cooperate with a microprocessor in order to perform one of the methods described herein. Generally, the methods are preferably performed by any hardware apparatus.

The apparatus described herein may be implemented using a hardware apparatus, or using a computer, or using a combination of a hardware apparatus and a computer.

The methods described herein may be performed using a hardware apparatus, or using a computer, or using a combination of a hardware apparatus and a computer.

In the foregoing Detailed Description, it can be seen that various features are grouped together in examples for the purpose of streamlining the disclosure. This method of disclosure is not to be interpreted as reflecting an intention that the claimed examples require more features than are expressly recited in each claim. Rather, as the following claims reflect, subject matter may lie in less than all features of a single disclosed example. Thus the following claims are hereby incorporated into the Detailed Description, where each claim may stand on its own as a separate example. While each claim may stand on its own as a separate example, it is to be noted that, although a dependent claim may refer in the claims to a specific combination with one or more other claims, other examples may also include a combination of the dependent claim with the subject matter of each other dependent claim or a combination of each feature with other dependent or independent claims. Such combinations are proposed herein unless it is stated that a specific combination is not intended. Furthermore, it is intended to include also features of a claim to any other independent claim even if this claim is not directly made dependent to the independent claim.

The above described embodiments are merely illustrative for the principles of the present disclosure. It is understood that modifications and variations of the arrangements and the details described herein will be apparent to others skilled in the art. It is the intent, therefore, to be limited only by the scope of the pending patent claims and not by the specific details presented by way of description and explanation of the embodiments herein.

What is claimed is:

1. A gas sensing device, comprising:
   a sensing unit for sensing a target gas, the sensing unit comprising a carbon-based sensing layer sensitive to the target gas;
   a controller unit, configured for monitoring an exposure of the sensing layer to the target gas, initializing a recovery sequence for the sensing unit depending on the exposure of the sensing unit to the target gas, and determining information about an oxidation of the sensing layer caused during the recovery sequence; and
   a heating electrode for heating the sensing layer during the recovery sequence.

2. The gas sensing device according to claim 1, wherein the sensing unit is configured for providing a measurement signal in dependence on a concentration of the target gas within an environment to which the sensing layer is exposed, and
   wherein the controller unit is configured for monitoring the exposure of the sensing layer to the target gas by evaluating the measurement signal.

3. The gas sensing device according claim 1, wherein the controller unit is configured for
   determining information about an accumulated exposure of the sensing layer to the target gas over a time period, and
   initializing the recovery sequence in dependence on the information about the accumulated exposure.

4. The gas sensing device according to claim 3, wherein the controller unit is configured for initializing the recovery sequence if the accumulated exposure of the sensing layer to the target gas exceeds a first threshold.

5. The gas sensing device according to claim 1, wherein the controller unit is configured for selecting a time instance for initializing the recovery sequence under consideration of an indication for a concentration of a specific target gas at the time instance.

6. The gas sensing device according claim 5, wherein the controller unit is configured for initializing the recovery sequence at a time instance for which the indication for the concentration of the specific target gas indicates a concentration of the specific target gas below a second threshold.

7. The gas sensing device according to claim 4, wherein the controller unit is configured for
   obtaining an indication for a concentration of a specific target gas, and
   if the information about the accumulated exposure indicates that the accumulated exposure of the sensing layer over the time period exceeds a first threshold,
   initializing the recovery sequence at a time for which the indication for the concentration of the specific target gas indicates a concentration of the specific target gas below a second threshold.

8. The gas sensing device according to claim 5, wherein the controller unit is configured for
   initializing the recovery sequence, if the information about the accumulated exposure indicates that the accumulated exposure of the sensing layer over the time period exceeds a third threshold.

9. The gas sensing device according to claim 1, wherein the controller unit is configured for
   determining information about an accumulated exposure of the sensing layer to a specific target gas during the recovery sequence, and
   initializing a functionality test sequence, if the information about the accumulated exposure to the specific target gas indicates, that an accumulated exposure of the sensing layer to the specific target gas during one or more recovery sequences exceeds a fourth threshold.

10. The gas sensing device according to claim 9, wherein the functionality test sequence comprises determining a baseline value of the sensing unit, and comparing the baseline value to one or more previously determined baseline values.

11. The gas sensing device according to claim 9, wherein the functionality test sequence comprises determining information about a concentration of a further specific target gas during a specific time period, and comparing the information about the concentration of the further specific target gas to previously determined information about a concentration of the further specific target gas during one or more further specific time periods.

12. The gas sensing device according to claim 11, wherein the sensing unit is configured for providing a measurement signal in dependence on a concentration of the target gas, and wherein the gas sensing device comprises a signal calibration unit for determining a calibrated measurement value based on the measurement signal,
  wherein the gas sensing device is configured for adjusting the determination of the calibrated measurement value if the functionality test sequence indicates
    a deviation between a baseline value and previously determined baseline values, and/or
    a deviation between the information about the concentration of the further specific target gas and the previously determined information about the concentration of the further specific target gas.

13. The gas sensing device according to claim 1, wherein the recovery sequence comprises heating the sensing layer of the sensing unit to a predetermined temperature which is different from a temperature of the sensing layer during a default operation mode of the gas sensing device.

14. The gas sensing device according to claim 1, further comprising:
  a further sensing unit, the further sensing unit comprising a further sensing layer which is sensitive to a further target gas; and
  a heating electrode for heating the further sensing layer during the recovery sequence.

15. The gas sensing device according to claim 1, the sensing layer comprises graphene, and wherein the target gas is ozone ($O_3$).

16. A method for operating a carbon-based gas sensing device, comprising:
  monitoring an exposure of a sensing unit of the gas sensing device to a target gas; and
  initializing a recovery sequence for the sensing unit depending on the exposure of the sensing unit to the target gas, wherein the recovery sequence comprises heating a sensing layer of the sensing unit, wherein the sensing layer comprises a carbon-based material; and
  determining information about an oxidation of the sensing layer caused during the recovery sequence.

17. The method of claim 16, further comprising:
  determining information about an accumulated exposure of the sensing layer to the target gas over a time period; and
  initializing the recovery sequence in dependence on the information about the accumulated exposure, wherein a controller unit is configured for initializing the recovery sequence if the accumulated exposure of the sensing layer to the target gas exceeds a first threshold.

18. The method of claim 17, wherein the sensing layer comprises graphene, and wherein the target gas is ozone ($O_3$).

19. A gas sensing device, comprising:
  a sensing unit for sensing a target gas comprising ozone ($O_3$), the sensing unit comprising a carbon-based sensing layer comprising graphene flakes that is sensitive to the target gas;
  a controller unit, configured for monitoring an exposure of the sensing layer to the target gas, initializing a recovery sequence for the sensing unit depending on the exposure of the sensing unit to the target gas, and determining information about an oxidation of the sensing layer caused during the recovery sequence; and
  a heating electrode for heating the sensing layer during the recovery sequence,
  wherein the sensing unit is configured for providing a measurement signal in dependence on a concentration of the target gas within an environment to which the sensing layer is exposed,
  wherein the controller unit is configured for monitoring the exposure of the sensing layer to the target gas by evaluating the measurement signal.

20. The gas sensing device of claim 19, wherein the sensing layer comprises graphene flakes.

* * * * *